(12) United States Patent
Sapi et al.

(10) Patent No.: US 8,697,419 B2
(45) Date of Patent: Apr. 15, 2014

(54) COMPOSITIONS AND METHODS FOR CULTURING SPIROCHETES

(71) Applicant: Advanced Laboratory Services, Inc., Sharon Hill, PA (US)

(72) Inventors: Eva T. Sapi, Madison, CT (US); Timothy Robert Schwartz, Atlanta, GA (US); Namrata Pabbati, Secane, PA (US)

(73) Assignee: Advanced Laboratory Services, Inc., Sharon Hill, PA (US)

( * ) Notice: Subject to any disclaimer, the term of this patent is extended or adjusted under 35 U.S.C. 154(b) by 0 days.

(21) Appl. No.: 13/626,450

(22) Filed: Sep. 25, 2012

(65) Prior Publication Data

US 2013/0084625 A1 Apr. 4, 2013

Related U.S. Application Data

(60) Provisional application No. 61/541,459, filed on Sep. 30, 2011.

(51) Int. Cl.
  *C12N 1/00* (2006.01)
  *C12N 1/20* (2006.01)
(52) U.S. Cl.
  USPC ............. 435/243; 435/253.6; 435/252.1
(58) Field of Classification Search
  USPC .................. 435/243, 252.1, 253.6
  See application file for complete search history.

(56) References Cited

U.S. PATENT DOCUMENTS

2001/0036658 A1* 11/2001 Phillips et al. ............. 435/253.6
2005/0042235 A1   2/2005 Korshus et al.

OTHER PUBLICATIONS

Kikuchi et al. Biological and Biochemical Characteristics of the Oral Spirochetes Isolated From the Focus of Marginal Periodontitis; Shigaku, vol. 76, No. 6 (1989) Abstract.*
Triaud et al. Evaluation of Automated Cell Culture Incubators; Journal of the Association for Laboratory Automation, vol. 8 (2003) pp. 82-86.*
Sinsky et al. Ear Punch Method for Detection and Isolation of Borrelia Burgdorferi From Rodents; Journal of Clinical Microbiology, vol. 27, No. 8 (1989) pp. 1723-1727.*
Aguero-Rosenfeld et al., "Diagnosis of lyme borreliosis," Clinical Microbiology Reviews, 18(3):484-509 (2005).
Aguero-Rosenfeld et al., "Evolution of the serologic response to Borrelia burgdorferi in treated patients with culture-confirmed erythema migrans," Journal of Clinical Microbiology, 34(1):1-9 (1996).
Alban et al., "Serum-starvation-induced changes in protein synthesis and morphology of Borrelia burgdorferi," Microbiology, 146(Pt 1):119-127 (2000).
Bacon et al., "Surveillance for Lyme disease--United States, 1992-2006," MMWR Surveillance Summaries, 57(10):1-9 (2008).
Barbour, "Isolation and cultivation of Lyme disease spirochetes." Yale Journal of Biology and Medicine, 57(4):521-525 (1984).
Battisti et al., "A system for site-specific genetic manipulation of the relapsing fever spirochete Borrelia hermsii," Methods in Molecular Biology, 431:69-84 (2008).
Boylan et al., "Borrelia burgdorferi membranes are the primary targets of reactive oxygen species," Molecular Microbiology, 68(3):786-799 (2008).
Bunikis et al., "Sequence typing reveals extensive strain diversity of the Lyme borreliosis agents Borrelia burgdorferi in North America and Borrelia afzelii in Europe," Microbiology, 150(Pt. 6):1741-1755 (2004).
Cabello et al., "Hidden in plain sight: Borrelia burgdorferi and the extracellular matrix," Trends in Microbiology, 15(8):350-354 (2007).
Casjens et al., "A bacterial genome in flux: the twelve linear and nine circular extrachromosomal DNAs in an infectious isolate of the Lyme disease spirochete *Borrelia burgdorferi*," Molecular Microbiolgy, 35(3):490-516 (2000).
Cerar et al., "Comparison of PCR methods and culture for the detection of Borrelia spp. in patients with erythema migrans," Clinical Microbiology and Infection, 14(7): 653-658 (2008).
Coleman et al., "Plasmin-coated borrelia Burgdorferi degrades soluble and insoluble components of the mammalian extracellular matrix," Infection and Immunity, 67(8):3929-3936 (1999).
Coyle et al., "Cerebrospinal fluid immune complexes in patients exposed to Borrelia burgdorferi: detection of Borrelia-specific and -nonspecific complexes," Annals of Neurology, 28(6):739-744 (1990).
De Martino et al., "Enhanced culture of Borrelia garinii and Borrelia afzelii strains on a solid BSK-based medium in anaerobic conditions," Research in Microbiology, 157(8):726-729 (2006).
Dumler, "Molecular diagnosis of Lyme disease: review and meta-analysis," Molecular Diagnosis, 6(1):1-11 (2001).
Grier, "The Difficulty of Culturing Spirochetes," 7 pages, downloaded Sep. 20, 2010, http://www.lymeneteurope.org/info/the-difficulty-of-culturing-spirochetes.
Hardin et al., "Immune complexes and the evolution of Lyme arthritis. Dissemination and localization of abnormal C1q binding activity," New England Journal of Medicine, 301(25):1358-1363 (1979).
Hastey et al., "Delays and diversions mark the development of B cell responses to Borrelia burgdorferi infection," Journal of Immunogy, 188(11):5612-5622 (2012).

(Continued)

*Primary Examiner* — Susan Hanley
*Assistant Examiner* — Paul Martin
(74) *Attorney, Agent, or Firm* — Ropes & Gray LLP

(57) ABSTRACT

The present invention relates to methods for culturing spirochetes, in particular *Borrelia burgdorferi*. The present invention also provides methods of identifying spirochetes present in a biological sample. The present invention further provides methods of diagnosing diseases cause by a spirochete infection, such as Lyme disease, syphilis, and multiple sclerosis. The present invention further provides methods for identifying spirochete susceptibilities to antimicrobials and antimicrobial compositions and cocktails. The present invention also provides methods for treating subjects suspected of having a spirochete infection.

42 Claims, 10 Drawing Sheets
(7 of 10 Drawing Sheet(s) Filed in Color)

(56) References Cited

OTHER PUBLICATIONS

Klempner et al., "Intralaboratory reliability of serologic and urine testing for Lyme disease," American Journal of Medicine, 110(3):217-219 (2001).

Klempner et al., "Two controlled trials of antibiotic treatment in patients with persistent symptoms and a history of Lyme disease,", New England Journal of Medicine, 34(2)5:85-92 (2001).

Liegner et al., "Recurrent erythema migrans despite extended antibiotic treatment with minocycline in a patient with persisting Borrelia burgdorferi infection," Journal of the American Academy of Dermatology, 28(2 Pt 2):312-314 (1993).

Liveris et al., "Comparison of five diagnostic modalities for direct detection of Borrelia burgdorferi in patients with early Lyme disease," Diagnostic Microbiology and Infectious Disease, 73(3):243-245 (2012).

Liveris et al., "Molecular typing of Borrelia burgdorferi sensu lato by PCR-restriction fragment length polymorphism analysis," Journal of Clinical Microbiology, 33(3):589-595 (1995).

Liveris et al., "Quantitative detection of Borrelia burgdorferi in 2-millimeter skin samples of erythema migrans lesions: correlation of results with clinical and laboratory findings," Journal of Clinical Microbiology, 40(4):1249-1253 (2002).

Maraspin et al., "Isolation of Borrelia burgdorferi sensu lato from blood of adult patients with borrelial lymphocytoma, Lyme neuroborreliosis, Lyme arthritis and acrodermatitis chronica atrophicans," Infection, 39(1):35-40 (2010).

Margos et al., "MLST of housekeeping genes captures geographic population structure and suggests a European origin of Borrelia burgdorferi," PNAS, 105(25): 8730-8735 (2008).

Marques et al., "Evaluation of a new culture medium for Borrelia burgdorferi," Journal of Clinical Microbiology, 38(11):4239-4241 (2000).

Marques, "Lyme disease: a review," Current Allergy and Asthma Reports, 10(1):13-20 (2010).

Mejri et al , "Immunosuppressive effects of ixodes ricinus tick saliva or salivary gland extracts on innate and acquired immune response of BALB/c mice," Parasitology Research, 88(2):192-197 (2002).

Miklossy et al., "Persisting atypical and cystic forms of Borrelia burgdorferi and local inflammation in Lyme neuroborreliosis," Journal of Neuroinflammation, 5:40-58 (2008).

Molloy et al., "False-positive results of PCR testing for Lyme disease," Clinical Infectious Diseases, 33(3):412-413 (2001).

Murgia et al., "Induction of cystic forms by different stress conditions in Borrelia burgdorferi," APMIS, 112(1):57-62 (2004).

Nadelman et al., "Failure to isolate Borrelia burgdorferi after antimicrobial therapy in culture-documented Lyme borreliosis associated with erythema migrans: report of a prospective study," American Journal of Medicine, 94(6):583-588 (1993).

Nelson et al., "Isolation and characterization of Borrelia burgdorferi from Illinois Ixodes dammini," Journla of Clinical Microbiology, 29(8):1732-1734 (1991).

Nelson, "Controversy brewing over Lyme disease testing," Lancet Infectious Disease, 5:605 (2005).

Nocton et al., "Detection of Borrelia burgdorferi DNA by polymerase chain reaction in cerebrospinal fluid in Lyme neuroborreliosis," Journal of Infectious Disease, 174(3):623-627 (1996).

Nowakowski et al., "Laboratory diagnostic techniques for patients with early Lyme disease associated with erythema migrans: a comparison of different techniques," Clinical Infectious Diseases, 33(12):2023-2027 (2001).

Phillips et al., "A proposal for the reliable culture of Borrelia burgdorferi from patients with chronic Lyme disease, even from those previously aggressively treated," Infection, 26(6):364-367 (1998).

Pollack et al., "Standardization of medium for culturing Lyme disease spirochetes," Journal of Clinical Microbiology, 31(5):1251-1255 (1993).

Preac-Mursic et al., "Culture of Borrelia burgdorferi on six solid media," European Journal of Clinical Microbiology and Infectious Diseases, 10(12):1076-1079 (1991).

Qiu et al., "Wide distribution of a high-virulence Borrelia burgdorferi clone in Europe and North America," Emerging Infectious Diseases, 14(7):1097-1104 (2008).

Rauter et al., "Critical evaluation of urine-based PCR assay for diagnosis of Lyme borreliosis," Clinical and Diagnostic Laboratory Immunology, 12(8):910-917 (2005).

Rodríguez et al., "Evaluation of a modified culture medium for Borrelia burgdorferi sensu lato," Memórias do Instituto Oswaldo Cruz, Rio de Janeiro, 102(8): 999-1002 (2007).

Sapi, et al., "Evaluation of in-vitro antibiotic susceptibility of different morphological forms of Borrelia burgdorferi," Infectection and Drug Resistance, 4: 97-113 (2011).

Schuijt et al., "A tick mannose-binding lectin inhibitor interferes with the vertebrate complement cascade to enhance transmission of the lyme disease agent," Cell Host and Microbe, 10(2):136-146 (2011).

Schutzer et al., "Sequestration of antibody to Borrelia burgdorferi in immune complexes in seronegative Lyme disease," Lancet, 335(8685):312-315 (1990).

Schwartz et al., "Diagnosis of early Lyme disease by polymerase chain reaction amplification and culture of skin biopsies from erythema migrans lesions," Journal of Clinical Microbiology, 30(12): 3082-3088 (1992).

Seshu et al., "Dissolved oxygen levels alter gene expression and antigen profiles in Borrelia burgdorferi," Infection and Immunity, 72(3):1580-1586 (2004).

Stanek et al., "Lyme borreliosis," Lancet, 379(9814):461-73 (2012).

Steere et al., "Prospective study of serologic tests for lyme disease," Clinical Infectious Diseases, 47(2):188-195 (2008).

Steere et al., "Treatment of Lyme arthritis," Arthritis & Rheumatism 37(6):878-888 (1994).

Wallach et al., "Circulating Borrelia burgdorferi in patients with acute Lyme disease: results of blood cultures and serum DNA analysis," Journal of Infectious Disease, 168(6):1541-1543 (1993).

Wang et al., "Genetic diversity of ospC in a local population of Borrelia burgdorferi sensu stricto," Genetics 151(1):15-30 (1999).

Weisburg et al., "16S ribosomal DNA amplification for phylogenetic study," J Bacteriol 173(2): 697-703 (1991).

Wormser et al., "Borrelia burgdorferi genotype predicts the capacity for hematogenous dissemination during early Lyme disease," Journal of Infectious Diseases, 198(9):1358-1364 (2008).

Wormser et al., "Comparison of the yields of blood cultures using serum or plasma from patients with Lyme disease," Journal of Clinical Microbiology, 38(4):1648-1650 (2000).

Wormser et al., "Effect of Borrelia burgdorferi genotype on the sensitivity of C6 and 2-tier testing in North American patients with culture-confirmed Lyme disease," Clinical Infectious Diseases, 47(7):910-914 (2008).

Wormser et al., "The clinical assessment, treatment, and prevention of lyme disease, human granulocytic anaplasmosis, and babesiosis: clinical practice guidelines by the Infectious Diseases Society of America," Clinical Infectious Diseases, 43(9):1089-134 (2006).

Wormser et al., "Yield of large-volume blood cultures in patients with early Lyme disease," Journal of Infectious Diseases, 184(8):1070-1072 (2001).

Zambrano et al., "Borrelia burgdorferi binds to, invades, and colonizes native type I collagen lattices," Infection and Immunology, 72(6):3138-3146 (2004).

Zhong et al., "Detection and preliminary characterization of circulating immune complexes in patients with Lyme disease," Medical Microbiology and Immunology, 186(2-3):153-158 (1997).

Muellegger et al., "No detection of Borrelia burgdorferi-specific DNA in erythema migrans lesions after minocycline treatment," Archives in Dermatology, 131(6):678-682 (1995).

Binek et al., Physiological properties and classification of strains of Treponema sp. isolated from pigs in Poland,Comparative Immunology, Microbiology & Infectious Diseases, 7(3-4):141-148 (1984).

Heroldova et al., "Growth parameters of Borrelia burgdorferi sensu stricto at various temperatures.," Zentrallblatt fur Bakeriaologie, 288(4):451-455 (1998).

\* cited by examiner

COMPOSITIONS AND METHODS FOR CULTURING SPIROCHETES

CROSS-REFERENCE TO RELATED APPLICATIONS

This application claims the benefit of U.S. Provisional Patent Application Ser. No. 61/541,459, filed Sep. 30, 2011, which is herein incorporated by reference in its entirety.

FIELD OF THE INVENTION

The present invention relates to in vitro methods of culturing spirochetes.

BACKGROUND OF THE INVENTION

Difficulties in culturing spirochetes, including *Borrelia burgdorferi*, *Borrelia recurrentis* and *Treponema pallidum*, have created unique challenges in studying, diagnosing and treating the diseases associated with these microorganisms, such as Lyme disease, relapsing fever, syphilis and multiple sclerosis.

Lyme disease, for example, is an infectious disease caused by infection with *Borrelia burgdorferi*, typically associated with a tick bite. Lyme disease presents with a multitude of variable symptoms, including fever, headache, fatigue, depression, and muscle soreness. The hallmark of Lyme disease is a bullseye-shaped skin rash, which develops in a majority of patients shortly after the tick bite. Despite this characteristic symptom, Lyme disease is routinely misdiagnosed as the flu, Alzheimer's disease, Parkinson's disease ADD/ADhD, autism, juvenile arthritis, rheumatoid arthritis, reactive arthritis, infectious arthritis, osteoarthritis, fibromyalgia, Raynaud's Syndrome, chronic fatigue syndrome, interstitial cystis, gastroesophageal reflux disease, Fifth Disease, multiple sclerosis, scleroderma, lupus, early ALS, Crohn's disease, Ménières syndrome, Sjogren's syndrome, irritable bowel syndrome, colitis, prostatitis, psychiatric disorders, bipolar, depression, encephalitis, sleep disorders, or thyroid disease.

In view of the complex and variable symptoms that present in spirochete infections, such as Lyme disease, the most reliable method of diagnosis is direct identification of the invasive spirochete. In many cases, identification of an invasive spirochete requires culturing the spirochete from a biological sample, such as a blood sample or a skin punch.

Attempts to culture spirochetes have yielded inconsistent results. For example, a method purported to successfully culture and identify *Borrelia burgdorferi* in over 90% of patients suffering from Lyme disease (Phillips et al., *Infection*, (1998) 26(6):364-367) could not be repeated in other clinics (Marques et al, *J. Clin. Microb.*, (2000) 38(11):4239-4241). Such discrepancies have helped fuel the controversial debate between medical experts about the existence of chronic Lyme disease (see, e.g., Grant, E. "Lyme Disease Controversy Comes to the Capitol" *NHPR News*, Feb. 1, 2010, available at www.nhpr.org/node/29157).

Further, spirochete cultures typically need to be cultured for 3-4 weeks before diagnostic tests or genotyping can be performed. Most other bacterial infections can be diagnosed within hours, not weeks. Accordingly, patients suffering from a spirochete infection must suffer for weeks or months before their infection can be successfully identified and treated. Thus, a reliable culture method with a shorter incubation time can help in the rapid diagnosis and identification of a treatment plan more likely to succeed.

SUMMARY OF THE INVENTION

The present invention is directed to improved compositions and methods for culturing spirochetes. A first aspect of the invention provides a composition for culturing spirochetes. In some embodiments, the composition comprises a spirochete-supporting medium, serum, a reducing agent and an antibiotic.

The spirochete-supporting medium may be BSK, BSK-H, BSK-II, or MPM medium, preferably BSK-H. In some embodiments, the serum is rabbit serum. The serum may be present at a concentration of about 6-12%, e.g., 12%.

The reducing agent may be dithiothreitol (DTT), e.g., at a concentration of 0.1-100 µg/ml, such as 0.145 µg/ml or 100 µg/ml. Optionally, the growth-control antibiotic is rifampicin, e.g., (1) present at a concentration of 1 µg/ml or (2) present in the form of a rifampicin antibiotics disc.

In a preferred embodiment, the composition comprises BSK-H medium, 12% rabbit serum, 0.145 µg/ml DTT and 1 µg/ml rifampicin. In another preferred embodiment, the composition comprises BSK-H medium, 12% rabbit serum, 0.145 µg/ml DTT and a rifampicin antibiotic disc.

In a preferred embodiment, the composition comprises BSK-H medium, 12% rabbit serum, 100 µg/ml DTT and 1 µg/ml rifampicin. In another preferred embodiment, the composition comprises BSK-H medium, 12% rabbit serum, 100 µg/ml DTT and a rifampicin antibiotic disc.

The composition may further comprise a spirochete, such as *Borrelia*, *Treponema*, *Brachyspira* and *Leptospira*. The spirochete may be selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

A second aspect of the invention provides an in vitro method for culturing a spirochete. The method provides a short-term culture method and, optionally, a long-term culture method. In some embodiments the method comprises inoculating a spirochete culture medium with a spirochete, wherein the spirochete culture medium is any of the compositions described above to generate a short-term culture, and incubating the short-term culture in a short-term culture vessel for about 4-6 days, optionally at about 32-36° C. (e.g., 34° C.) in about 3-5% $CO_2$ (e.g., 5% $CO_2$) and about 96-100% humidity (e.g., 100% humidity). The short-term culture vessel may be a polystyrene tube, optionally having a volume less than 5 ml, e.g., 2 ml. The short-term culture may have a volume of about 1.8 ml. Gas exchange between the short-term culture and the environment may occur, such as by incubation in a short-term culture vessel with a loose lid or a lid with a vent.

Optionally, the method further comprises transferring spirochete cells from the short-term culture into a long-term culture vessel comprising one or more solid supports with a matrix and a spirochete culture medium according to the compositions described above to generate a long-term culture, and incubating the long-term culture, optionally at about 32-36° C. (e.g., 34° C.) in about 3-5% $CO_2$ (e.g., 5% $CO_2$) and about 96-100% humidity (e.g., 100% humidity). The long-term culture may be incubated for about 4-8 weeks. Preferably, at least about $1\times10^5$ spirochete cells are transferred from the short-term culture to the long-term culture. The long-term culture vessel may be a Coplin jar. The matrix may be selected from collagen, fibronectin, laminin, peptidoglycan, elastin, and agarose, preferably collagen. The solid support may be a microscope slide, such as a collagen-coated slide. Gas exchange between the long-term culture and the environment may occur, such as by incubation in a long-term culture vessel with a loose lid or a lid with a vent.

In some embodiments, the spirochete is selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

The culture conditions can be applied to a biological sample, such as a sample that may contain a spirochete, e.g., to determine whether or not a live spirochete is present in the sample. In some embodiments, the sample is obtained from a subject, such as a human, possibly suffering from a spirochete infection. The sample may be obtained from a skin biopsy, cerebrospinal fluid, joint fluid or a blood sample. In some embodiments, the blood sample is drawn from the subject after noon. In some embodiments, the blood sample is stored for up to 24 hours in a VACUTAINER™ tube with no additive, a VACUTAINER™ tube with EDTA, or a sterile tube with spirochete-supporting medium, such as BSK-H. In some embodiments, the blood sample is incubated at room temperature for 2-3 hours prior to inoculation to separate the serum/plasma phase by sedimentation and the spirochete culture medium is inoculated with a portion of the serum/plasma phase. In some embodiments, the serum/plasma phase is further separated by centrifugation after sedimentation and before inoculation.

In some embodiments, the short-term or long-term culture is incubated in an anaerobic or microaerobic environment, e.g., obtained by culturing spirochetes in such that the culture media substantially fills the interior volume of the culture vessel (e.g., fills at least 50%, 60%, 70%, 80%, 90% or more of the culture vessel volume), candle extinction in a sealed jar, the loose-cap method, flushing with inert gas, and/or addition of an additional reducing agent, such as beta-mercaptoethanol, an iron-containing compound, amorphous ferrous sulfide, tris(2-carboxyethyl)phosphine, palladium chloride, sodium thioglycolate, cysteine×HCl, $Na_2S.9H_2O$, sodium dithionite, and an enzyme such as a mono- and/or di-oxygenase, and/or succinate.

A third aspect of the invention provides a method of identifying a spirochete. The method may comprise any of the spirochete culture methods discussed above along with a spirochete identification assay, such as an ELISA, a Western blot, an immunostaining assay (e.g., an immunofluorescence assay), the Gunderson test, PCR, and an antigen capture test. For example, the spirochete identification assay may comprise an immunostaining (e.g., immunofluorescence) assay or a PCR. Optionally, the antibody used in the immunostaining (e.g., immunofluorescence) assay is directed to a spirochete-specific marker (e.g., flagella, ospA, or ospC), preferably a marker that identifies a spirochete species or subspecies. The PCR reaction may use spirochete-specific primers (e.g., primers to amplify 16s rRNA, flagella, ospA, or ospC encoding sequences or any housekeeping gene), preferably primers that identify a spirochete species or subspecies.

The spirochete identification assay may be performed on spirochetes from the short-term culture. Alternatively, the spirochete identification assay may be performed on spirochetes from the long-term culture, such as cells on one or more matrix-coated support (e.g., collagen-coated slide). The matrix-coated support (e.g., collagen-coated slide) may be used in an immunostaining (e.g., immunofluorescence) assay or cells may be scraped from the matrix-coated support (e.g., collagen-coated slide) for DNA extraction for PCR and/or direct sequencing.

The spirochete can be obtained from an established cell line, an uncharacterized cell culture or a subject, preferably human, possibly suffering from a spirochete infection.

The spirochete may be selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

A fourth aspect of the invention provides a method of diagnosing a spirochete infection in a subject. The method may comprise any of the spirochete culture methods discussed above, wherein the spirochete is obtained from a sample from a subject (such as a human) possibly suffering from a spirochete infection, along with a spirochete detection assay, such as dark-field microscopy, fluorescent microscopy (preferably with a fluorescent dye, such as acridine orange), an ELISA, a Western blot, an immunostaining assay (e.g., an immunofluorescence assay), the Gunderson test, PCR, and an antigen capture test, wherein detection of the spirochete indicates that the subject is suffering from a spirochete infection. For example, the spirochete detection assay may comprise dark-field microscopy, fluorescent microscopy (with a fluorescent dye, such as acridine orange), an immunostaining (e.g., immunofluorescence) assay or PCR. Preferably, the dark-field microscopy or fluorescent microscopy shows the spirochetal structure of the spirochete. Optionally, the antibody used in the immunostaining (e.g., immunofluorescence) assay is directed to a spirochete-specific marker (e.g., flagella, ospA, or ospC), preferably a marker that identifies a spirochete species or subspecies. The PCR reaction may use spirochete-specific primers (e.g., primers to amplify 16s rRNA, flagella, ospA, or ospC encoding sequences or any housekeeping gene), preferably primers that identify a spirochete species or subspecies. The acridine orange stain may be at pH 4.0 in acetate buffer.

The spirochete detection assay may be performed on spirochetes from the short-term culture. Alternatively, the spirochete detection assay may be performed on spirochetes from the long-term culture, such as cells on one or more matrix-coated support (e.g., collagen-coated slide). The matrix-coated support (e.g., collagen-coated slide) may be used in dark-field microscopy, fluorescent microscopy, an immunostaining (e.g., immunofluorescence) assay or cells may be scraped from the matrix-coated support (e.g., collagen-coated slide) for DNA extraction for PCR and/or direct sequencing.

The spirochete may be selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

A fifth aspect of the invention provides a method of identifying the antibiotic sensitivity of a spirochete. In some embodiments, the method comprises inoculating a spirochete culture medium with a spirochete, wherein the spirochete culture medium is any of the compositions discussed above; incubating the inoculated medium for about 4-6 days, optionally at about 32-36° C. in about 5% $CO_2$ and about 96-100% humidity; transferring the cultured spirochetes into a secondary culture comprising a test antibiotic, wherein inhibition of the growth or proliferation, or even death, of the spirochete indicates that the spirochete is sensitive to the test antibiotic. The secondary culture can be a short-term culture or a long-term culture as described above. The test antibiotic is selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid.

Inhibition of growth or proliferation may be detected by any suitable method. For example, cellular growth assays include directly counting the spirochete cells using a bacterial counting chamber and dark field microscopy. Alternatively, a bacterial viability assay may be used to determine the ratio of live and dead spirochetes. The various morphological forms of the spirochete may also be scored.

In some embodiments, the spirochete is selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

The spirochete may be obtained from an established cell line, an uncharacterized cell culture, or a sample from a subject, such as a human, suffering from a spirochete infection. The sample can be obtained from the subject by any of the methods discussed above.

A sixth aspect of the invention provides a method of treating a subject suffering from a spirochete infection. In some embodiments, the method comprises inoculating a spirochete culture medium with a sample from the subject, wherein the spirochete culture medium is any of the compositions discussed above; incubating the inoculated medium for 4-6 days, optionally at about 32-36° C. in about 5% $CO_2$ and about 96-100% humidity; transferring the cultured spirochetes into a secondary culture comprising a test antibiotic, wherein inhibition of the growth or proliferation, or even death, of the spirochete indicates that the spirochete is sensitive to the test antibiotic and administering an effective amount of the test antibiotic to the subject. The secondary culture can be a short-term culture or a long-term culture as described above. The test antibiotic is selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid. The sample can be obtained from the subject by any of the methods discussed above.

Inhibition of growth or proliferation may be detected by any suitable method. For example, cellular growth assays include directly counting the spirochete cells using a bacterial counting chamber and dark field microscopy. Alternatively, a bacterial viability assay may be used to determine the ratio of live and dead spirochetes. The various morphological forms of the spirochete may also be scored.

In some embodiments, the spirochete is selected from *Borrelia burgdorferi*, *Borrelia recurrentis*, *Treponema pallidum*, *Brachyspira pilosicoli* and *Brachyspira aalborgi*, preferably *Borrelia burgdorferi*, such as *Borrelia burgdorferi* sensu lato.

Particular embodiments of the invention are set forth in the following numbered paragraphs:

1. A composition for culturing spirochetes comprising a spirochete-supporting medium, serum, a reducing agent, and an antibiotic.
2. The composition according to paragraph 1, wherein the spirochete-supporting medium is selected from BSK-H medium, BSK-II and MPM medium.
3. The composition according the paragraph 1 or 2, wherein the serum is rabbit serum.
4. The composition according to any one of paragraphs 1-3, wherein the serum concentration is about 6-12%.
5. The composition of paragraph 4, wherein the serum concentration is 12%.
6. The composition according to any one of paragraphs 1-5, wherein the reducing agent is DTT.
7. The composition according to paragraph 1-6, wherein the reducing agent is present at a concentration of 0.1-100 µg/ml, such as 0.145 µg/ml or 100 µg/ml.
8. The composition according to any one of paragraphs 1-7, wherein the antibiotic is rifampicin.
9. The composition according to paragraph 8, wherein the rifampicin is present at a concentration of 1 µg/ml.
10. The composition according to paragraph 8, wherein the rifampicin is present in an antibiotics disc.
11. The composition according to paragraph 1, wherein the composition comprises BSK-H, 12% rabbit serum, 0.145 µg/ml DTT, and 1 µg/ml rifampicin.
12. The composition according to paragraph 1, wherein the composition comprises BSK-H, 12% rabbit serum, 0.145 µg/ml DTT, and a rifampicin antibiotic disc.
13. The composition according to paragraph 1, wherein the composition comprises BSK-H, 12% rabbit serum, 100 µg/ml DTT, and 1 µg/ml rifampicin.
14. The composition according to paragraph 1, wherein the composition comprises BSK-H, 12% rabbit serum, 100 µg/ml DTT, and a rifampicin antibiotic disc.
15. The composition according to any one of paragraphs 1-14, wherein the composition further comprises a spirochete, such as *Borrelia*, *Treponema*, *Brachyspira* and *Leptospira*.
16. The composition according to paragraph 15, wherein the spirochete is selected from *Borrelia burgdorferi*, *Borrelia recurrentis*, *Treponema pallidum*, *Brachyspira pilosicoli* and *Brachyspira aalborgi*.
17. The composition according to paragraph 16, wherein the spirochete is *Borrelia burgdorferi*, such as *Borrelia burgdorferi* sensu lato.
18. An in vitro method of culturing a spirochete comprising:
    (1) inoculating a composition according to any one of paragraphs 1-14 with the spirochete to generate a short-term culture; and
    (2) incubating the short-term culture in a short-term culture vessel for about 4-6 days.
19. The method according to paragraph 18, wherein the short-term culture is incubated at about 32-36° C. in about 3-5% $CO_2$ and about 96-100% humidity.
20. The method according to paragraph 18 or 19, wherein the short-term culture vessel is a polystyrene tube.
21. The method according to paragraph 20, wherein the polystyrene tube has a volume less than about 5 ml.
22. The method according to paragraph 21, wherein the polystyrene tube has a volume of about 2 ml.
23. The method according to paragraph 22, wherein the short-term culture has a volume of about 1.8 ml.
24. The method according to any one of paragraphs 18-23, wherein gas exchange between the short-term culture and the environment is permitted, optionally to a limited extent.
25. The method according to paragraph 24, wherein the short-term culture vessel has a lid and the lid either (1) is loose or (2) comprises a vent.
26. The method according to any one of paragraphs 18-25, wherein the short-term culture is incubated at 34° C.
27. The method according to any one of paragraphs 18-26, wherein the short-term culture is incubated in about 5% $CO_2$.
28. The method according to any one of paragraphs 18-27, wherein the short-term culture is incubated in about 100% humidity.
29. The method according to any one of paragraphs 18-28, further comprising:
    (3) transferring spirochete cells into a long-term culture vessel, wherein the long-term culture vessel contains one or more solid supports coated with a matrix and a spirochete culture medium, e.g., as defined according to any one of paragraphs 1-12, to generate a long-term culture;
(4) incubating the long term culture.
30. The method according to paragraph 29, wherein the long-term culture is incubated at about 32-36° C. in about 3-5% $CO_2$ and about 96-100% humidity.
31. The method according to paragraph 29 or 30, wherein the long-term culture is incubated for at least about 4-8 weeks.
32. The method according to any one of paragraphs 29-31, wherein at least about $1 \times 10^5$ spirochete cells are transferred from the short-term culture into long-term culture.
33. The method according to any one of paragraphs 29-32, wherein the long-term culture vessel is a Coplin jar.
34. The method according to any one of paragraphs 29-33, wherein the matrix is selected from collagen, fibronectin, laminin, peptidoglycan, elastin, and agarose.
35. The method according to paragraph 34, wherein the matrix is collagen.
36. The method according to any one of paragraphs 29-35, wherein the solid support is a microscope slide.
37. The method according to paragraph 36, wherein the microscope slide is a collagen-coated slide.
38. The method according to any one of paragraphs 29-37, wherein gas exchange between the long-term culture medium and the environment is permitted, optionally to a limited extent.
39. The method according to paragraph 38, wherein the long-term culture vessel has a lid that either (1) is loose or (2) comprises a vent.
40. The method according to any one of paragraphs 29-39, wherein the long-term culture is incubated at 34° C.
41. The method according to any one of paragraphs 29-40, wherein the long-term culture is incubated in about 5% $CO_2$.
42. The method according to any one of paragraphs 29-41, wherein the long-term culture is incubated in about 100% humidity.
43. The method according to any one of paragraphs 18-42, wherein the spirochete is *Borrelia burgdorferi*, *Borrelia recurrentis*, *Treponema pallidum*, *Brachyspira pilosicoli* or *Brachyspira aalborgi*.
44. The method according to paragraph 43, wherein the spirochete is *Borrelia burgdorferi*, such as *Borrelia burgdorferi* sensu lato.
45. The method according to any one of paragraphs 18-44, wherein the spirochete is obtained from a sample from a subject suffering from a spirochete infection.
46. The method according to paragraph 45, wherein the subject is human.
47. The method according to paragraph 45 or 46, wherein the sample is a skin biopsy, a cerebrospinal fluid sample, a joint fluid sample or a blood sample.
48. The method according to paragraph 47, wherein the blood sample is drawn after noon.
49. The method according to paragraph 47 or 48, wherein the blood sample is stored for up to 24 hours in a VACUTAINER™ tube with no additive, a VACUTAINER™ tube with EDTA, or a sterile tube with spirochete-supporting medium.
50. The method according to paragraph 49, wherein the spirochete-supporting medium is BSK-H.
51. The method according to any one of paragraphs 47-50, wherein the blood sample is incubated at room temperature for 2-3 hours prior to inoculation to separate the serum/plasma phase by sedimentation and the spirochete culture medium is inoculated with a portion of the serum/plasma phase.
52. The method according to paragraph 51, wherein the serum/plasma phase is further separated by centrifugation after sedimentation and before inoculation.
53. The method according to any one of paragraphs 18-52, wherein the inoculated medium is incubated in an anaerobic or microaerobic environment.
54. The method according to paragraph 53, wherein the anaerobic or microaerobic environment is obtained by culturing spirochetes in a culture volume that is about 90% of the culture vessel volume, candle extinction in a sealed jar, flushing with inert gas, or addition of an additional reducing agent.
55. The method according to paragraph 54, wherein the additional reducing agent is selected from beta-mercaptoethanol, an iron-containing compound, amorphous ferrous sulfide, tris(2-carboxyethyl)phosphine, palladium chloride, sodium thioglycolate, cysteine×HCl, $Na_2S.9H_2O$, sodium dithionite, and an enzyme such as a mono- and/or di-oxygenase, and/or succinate.
56. A method of identifying a spirochete in a subject comprising:
(1) culturing the spirochete by any of the methods according to paragraphs 18-55; and
(2) identifying the spirochete in an identification assay.
57. The method according to paragraph 56, wherein the identification assay is selected from an ELISA, a Western blot, an immunostaining assay, the Gunderson test, PCR, and an antigen capture test.
58. The method according to paragraph 57, wherein the immunostaining assay is an immunofluorescence assay.
59. The method according to paragraph 57 or 58, wherein the immunostaining assay utilizes an antibody directed to a spirochete-specific marker.
60. The method according to paragraph 59, wherein the antibody specifically binds a marker that identifies a spirochete species or subspecies.
61. The method according to paragraph 57, wherein the PCR uses spirochete-specific primers.
62. The method according to paragraph 61, wherein spirochete-specific primers amplify a sequence that identifies a spirochete species or subspecies.
63. The method according to any one of paragraphs 56-62, wherein the identification assay is performed after the short-term culture method.
64. The method according to any one of paragraphs 56-62, wherein the identification assay is performed after the long-term culture method.
65. The method according to paragraph 64, wherein the identification assay is performed on a matrix-coated support (e.g., a collagen-coated slide).
66. The method according to paragraph 65, wherein the matrix-coated support (e.g., a collagen-coated slide) is immunostained.
67. The method according to paragraph 65, wherein cells are scraped from the matrix-coated support (e.g., a collagen-coated slide) for DNA extraction and PCR.
68. The method according to any one of paragraphs 56-67, wherein the spirochete is obtained from an established cell line, an uncharacterized cell culture, or a sample from a subject suffering from a spirochete infection.
69. The method according to any one of paragraphs 56-68, wherein the spirochete is selected from *Borrelia burgdorferi*, *Borrelia recurrentis*, *Treponema pallidum*, *Brachyspira pilosicoli* and *Brachyspira aalborgi*.

70. The method according to paragraph 69, wherein the spirochete is *Borrelia burgdorferi*, such as *Borrelia burgdorferi* sensu lato.
71. A method of diagnosing a spirochete infection in a subject comprising:
    (1) culturing the spirochete by any of the methods according to paragraphs 18-55, wherein the spirochete is obtained from a sample from a subject possibly suffering from a spirochete infection; and
    (2) detecting the spirochete in a detection assay, wherein detection of the spirochete indicates that the subject is suffering from a spirochete infection.
72. The method according to paragraph 71, wherein the subject is a human.
73. The method according to paragraph 71 or 72, wherein the detection assay is selected from dark-field microscopy, fluorescent microscopy, an ELISA, a Western blot, an immunostaining assay, the Gunderson test, PCR, and an antigen capture test.
74. The method according to paragraph 73, wherein the spirochete is stained with a fluorescent dye for fluorescent microscopy.
75. The method according to paragraph 74, wherein the fluorescent dye is acridine orange.
76. The method according to paragraph 75, wherein the acridine orange is pH 4.0 and in acetate buffer.
77. The method according to any one of paragraphs 73-76, wherein the dark-field microscopy or the fluorescent microscopy shows the spirochetal structure of the spirochete.
78. The method according to paragraph 73, wherein the immunostaining assay is an immunofluorescence assay.
79. The method according to paragraph 73 or 78, wherein the immunostaining assay utilizes an antibody directed to a spirochete-specific marker.
80. The method according to paragraph 79, wherein the antibody specifically binds a marker that identifies a spirochete species or subspecies.
81. The method according to paragraph 73, wherein the PCR uses spirochete-specific primers.
82. The method according to paragraph 81, wherein spirochete-specific primers amplify a sequence that identifies a spirochete species or subspecies.
83. The method according to any one of paragraphs 71-82, wherein the identification assay is performed after the short-term culture method.
84. The method according to any one of paragraphs 71-82, wherein the identification assay is performed after the long-term culture method.
85. The method according to paragraph 84, wherein identification assay is performed on a matrix-coated support (e.g., a collagen-coated slide).
86. The method according to paragraph 85, wherein the matrix-coated support (e.g., a collagen-coated slide) is immunostained.
87. The method according to paragraph 86, wherein cells are scraped from the matrix-coated support (e.g., a collagen-coated slide) for DNA extraction for PCR and/or direct sequencing.
88. The method according to any one of paragraphs 71-87, wherein the spirochete is selected from *Borrelia burgdorferi*, *Borrelia recurrentis*, *Treponema pallidum*, *Brachyspira pilosicoli* and *Brachyspira aalborgi*.
89. The method according to paragraph 88, wherein the spirochete is *Borrelia burgdorferi*, such as *Borrelia burgdorferi* sensu lato.
90. A method of identifying the antibiotic sensitivity of a spirochete comprising:
    (1) inoculating a spirochete culture medium in a culture vessel with a spirochete, wherein the spirochete culture medium is a composition according to any one of paragraphs 1-14;
    (2) incubating the inoculated medium for about 4-6 days;
    (3) transferring the cultured spirochetes into a secondary culture comprising a test antibiotic; and
    (4) incubating the secondary culture, wherein inhibition of the growth or proliferation, or even death, of the spirochete indicates that the spirochete is sensitive to the test antibiotic.
91. The method according to paragraph 90, wherein the inoculated media is incubated at about 32-36° C. in about 3-5% $CO_2$ and about 96-100% humidity.
92. The method according to 90 or 91, wherein the secondary culture is incubated at about 32-36° C. in about 3-5% $CO_2$ and about 96-100% humidity.
93. The method according to any one of paragraphs 90-92, wherein the secondary culture is a short-term culture prepared according to any one of paragraphs 18-55 or a long-term culture prepared according to any one of paragraphs 28-55.
94. The method according to any one of paragraphs 90-93, wherein the test antibiotic is selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid.
95. The method according to any one of paragraphs 90-94, wherein cell growth, proliferation or death is evaluated in a cell proliferation assay or a cell death assay.
96. The method according to paragraph 95, wherein the cell proliferation assay comprises directly counting the spirochete cells in a bacterial counting chamber.
97. The method according to paragraph 95, wherein a bacterial viability assay is used to determine the ratio of live cells to dead cells.
98. The method according to any one of paragraphs 90-97, wherein the spirochete is selected from *Borrelia burgdorferi*, *Borrelia recurrentis*, *Treponema pallidum*, *Brachyspira pilosicoli* and *Brachyspira aalborgi*.
99. The method according to paragraph 98, wherein the spirochete is *Borrelia burgdorferi*, such as *Borrelia burgdorferi* sensu lato.
100. The method according to any one of paragraphs 90-99, wherein the spirochete is obtained from an established cell line, an uncharacterized cell culture, or a sample from a subject suffering from a spirochete infection.
101. A method of treating a subject suffering from a spirochete infection comprising
    (1) obtaining a sample from a subject suffering from a spirochete infection;
    (2) inoculating a spirochete culture medium the sample, wherein the spirochete culture medium is a composition according to any one of paragraphs 1-12;
    (3) incubating the inoculated medium for about 4-6 days;
    (4) transferring the cultured spirochetes into a secondary culture comprising a test antibiotic;
    (5) incubating the secondary culture, wherein inhibition of the growth or proliferation, or even death, of the spirochete indicates that the spirochete is sensitive to the test antibiotic; and (6) administering an effective amount of the test antibiotic to the subject.

102. The method according to paragraph 101, wherein the inoculated media is incubated at about 32-36° C. in about 3-5% $CO_2$ and about 96-100% humidity.

103. The method according to 101 or 102, wherein the secondary culture is incubated at about 32-36° C. in about 3-5% $CO_2$ and about 96-100% humidity.

104. The method according to any one of paragraphs 101-103, wherein the secondary culture is a short-term culture prepared according to any one of paragraphs 18-55 or a long-term culture prepared according to any one of paragraphs 28-55.

105. The method according to any one of paragraphs 101-104, wherein the test antibiotic is selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid.

106. The method according to any one of paragraphs 101-105, wherein cell growth, proliferation or death is evaluated in a cell proliferation assay or a cell death assay.

107. The method according to paragraph 106, wherein the cell proliferation assay comprises directly counting the spirochete cells in a bacterial counting chamber.

108. The method according to paragraph 107, wherein a bacterial viability assay is used to determine the ratio of live cells to dead cells.

109. The method according to any one of paragraphs 101-108, wherein the spirochete is selected from *Borrelia burgdorferi*, *Borrelia recurrentis*, *Treponema pallidum*, *Brachyspira pilosicoli* and *Brachyspira aalborgi*.

110. The method according to paragraph 109, wherein the spirochete is *Borrelia burgdorferi*, such as *Borrelia burgdorferi* sensu lato.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
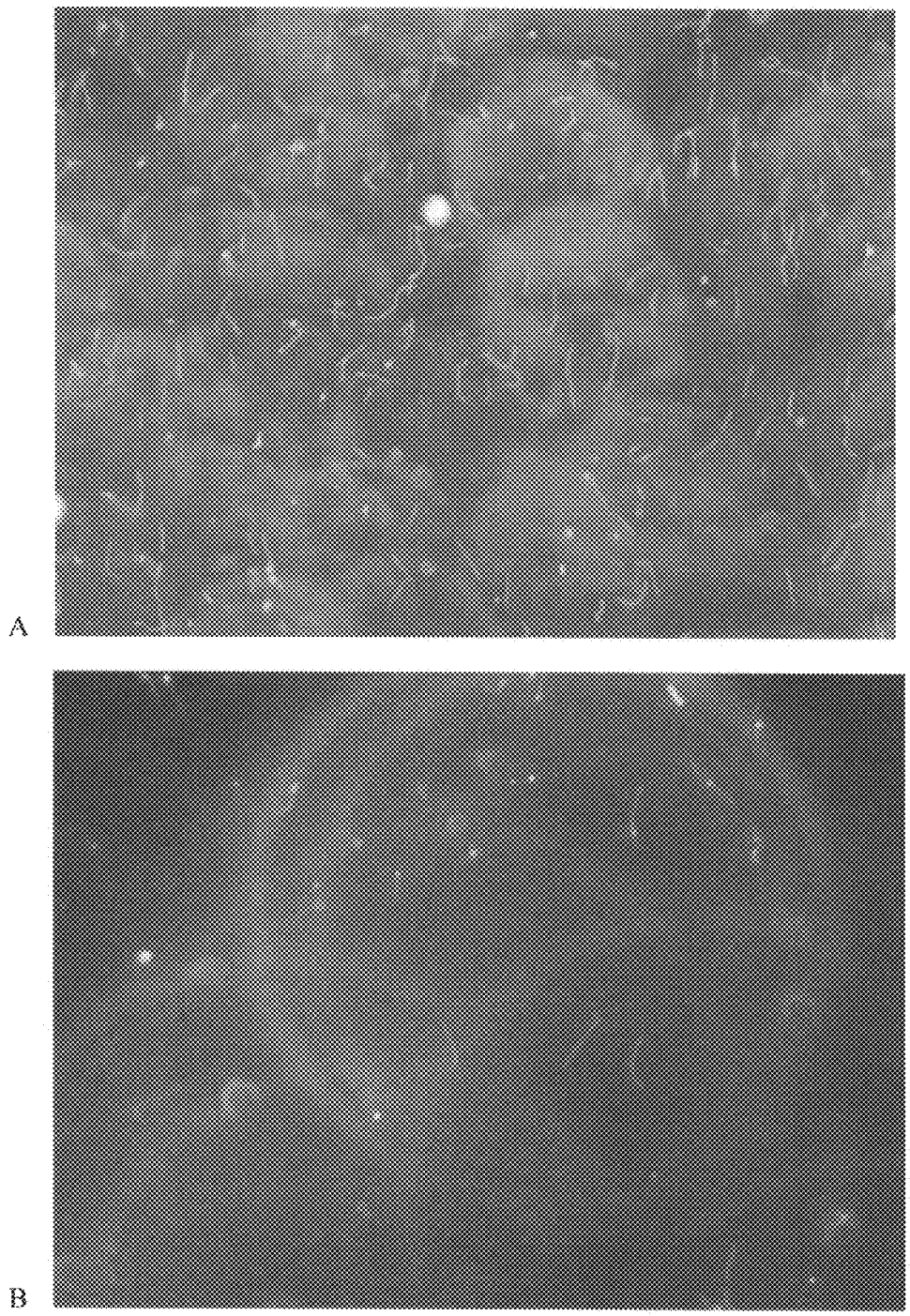
FIG. 1 shows B31 (*Borrelia burgdorferi*) cells, Passage 4, after 3-days growth in two different media. $5 \times 10^6$ cells were grown in 7 ml of BSK-H medium (panel A) in a 12 ml sterile glass tube and in 7 ml of MPM medium (panel B) in a 12 ml sterile glass tube. After 3 days incubation in $CO_2$ incubator at 32° C. with 5% CO2 and 100% humidity, spirochete growth was evaluated by dark-field microscopy.
Figure 2:
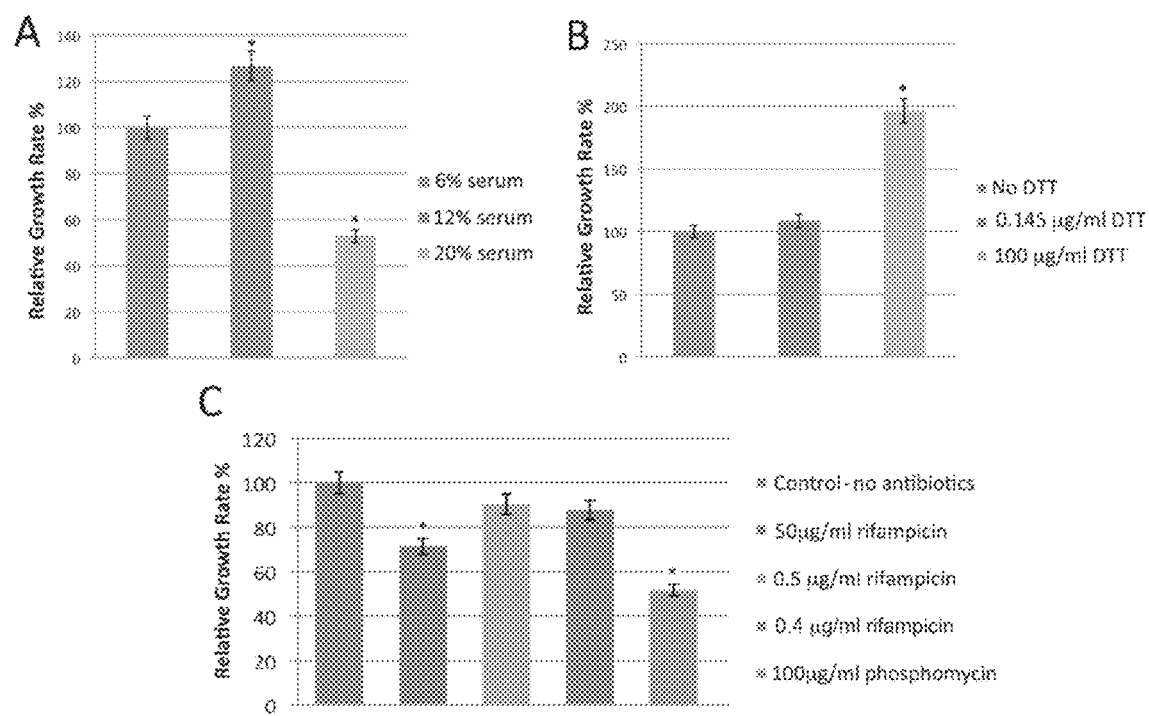
FIG. 2 shows the effect of different concentrations of rabbit serum (Panel A), DTT (Panel B) and antibiotic concentrations (Panel C) on the growth of *Borrelia burgdorferi* B31 strains. The cells were cultured for 6 days with different concentration of rabbit serum, DTT and antibiotics, as depicted, and cellular growth was evaluated by direct cell counting of motile spirochetes using dark field microscopy. Each set of data represents three independent experiments (mean±SD). Statistical significance was determined using two-sample paired t-test. The data *p-values<0.05 indicates statistical significance as related to control.
Figure 3:
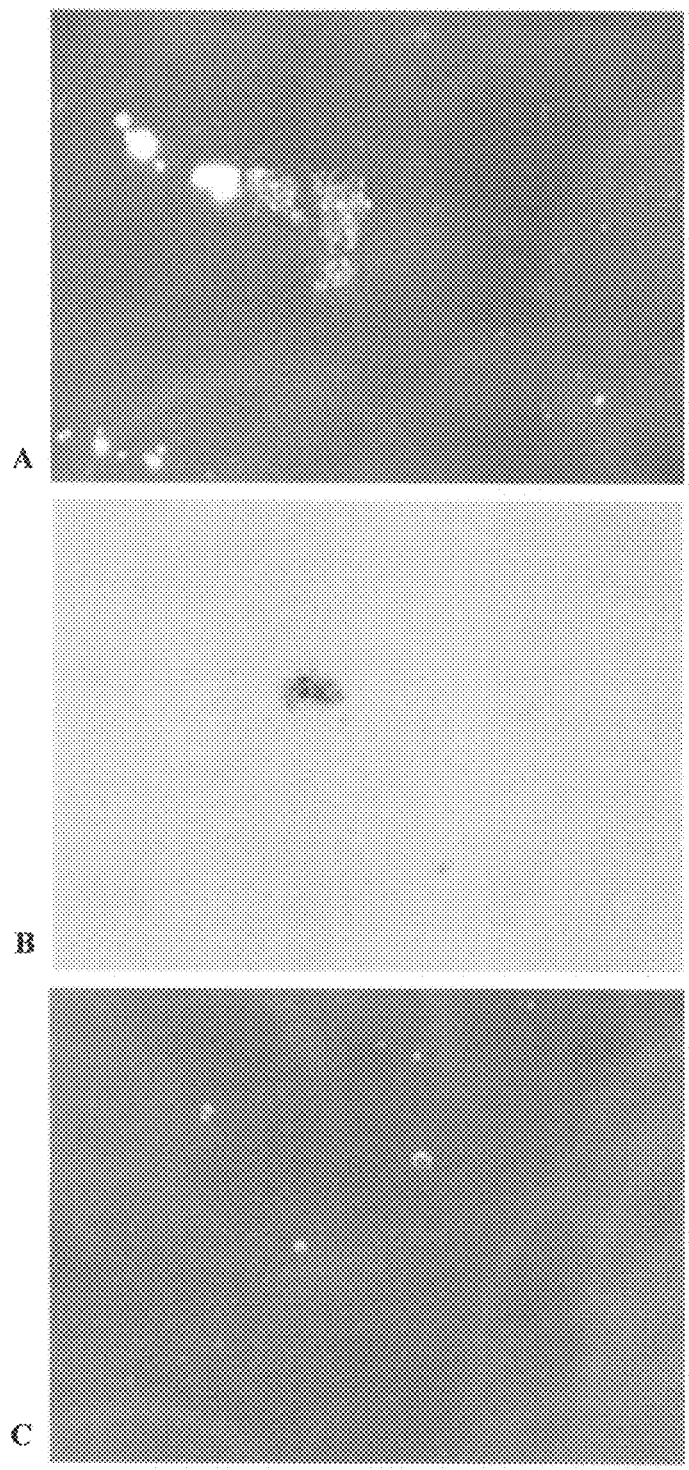
FIG. 3 shows the effect of microaerobic and anaerobic environments on spirochete growth. $1 \times 10^6$ B31 (*Borrelia burgdorferi*) cells, Passage 7, were cultured on solid BSK-II medium in 100 mm polystyrene Petri dishes and incubated in microaerobic and anaerobic environments. After 20 days, B31 colonies were observed on the plate incubated in the microaerobic environment at 34° C. with 5% $CO_2$ and 100% humidity in $CO_2$ incubator. Dark-field microscopy of colonies picked from the microaerobic plate demonstrated that the colonies had a spirochetal structure (Panel A). B31 cells picked from the microaerobic plate were also stained with 0.1% w/v crystal violet, and their spirochetal structure was observed by bright-field microscopy (Panel B). Plates incubated at anaerobic condition at 34° C. with 5% $CO_2$ and 100% humidity in $CO_2$ incubator for 20 days resulted in no visible colonies. The surface of the anaerobic plate was scraped into culture media, which was examined by dark field microscopy. No spirochetal cells were observed. (Panel C). Magnification 200×.

In order that the invention described herein may be fully understood, the following detailed description is set forth.

Unless defined otherwise, all technical and scientific terms used herein have the same meaning as those commonly understood by one of skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "anaerobic" refers to an environmental condition in which oxygen is not present. Anaerobic conditions include conditions completely devoid of oxygen and conditions with minute concentrations of oxygen (i.e. "microaerobic" conditions). "Microaerobic" conditions include conditions with oxygen concentration less than 20%, such as 0-5%, 0-10%, or 0-15%. Microaerobic conditions can include conditions with about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% oxygen. Anaerobic conditions may be generated using candle extinction in a sealed jar, the loose-cap method, flushing with inert gas such as nitrogen, or addition of an additive, such as an additional reducing agent, that creates an anaerobic environment.

The term "anaerobe" refers to an organism that does not require the presence of oxygen in the environment for growth. Oxygen may be harmful to anaerobes. Anaerobes include both "obligate anaerobes," which cannot tolerate the presence of oxygen, and "microaerophiles," which can tolerate small amounts of oxygen.

The term "loose cap method" refers to a method of culture incubation wherein gas exchange occurs between the culture medium and the environment. Such gas exchange may be achieved by incubating a culture vessel with its cap slightly loosened or using a culture vessel with a vented cap. Preferably, this method allows for minimal gas exchange between the culture medium and the environment.

The term "reducing agent" refers to element or compound in a reduction-oxidation (redox) reaction that donates an electron to another species. Without being bound by theory, it is hypothesized that reducing agents help anaerobic organisms tolerate the presence of oxygen in the environment. Non-limiting examples of reducing agents include dithiothreitol (DTT), beta-mercaptoethanol, an iron-containing compound, amorphous ferrous sulfide, tris(2-carboxyethyl)phosphine, palladium chloride, sodium thioglycolate, cysteine×HCl, $Na_2S.9H_2O$, sodium dithionite, and an enzyme such as a mono- and/or di-oxygenase, and/or succinate.

The term "spirochete" refers to a phylum of gram-negative bacteria characterized by a long, helical-coil shape. There are several genera of spirochetes, such as *Borrelia*, *Treponema*, *Brachyspira* and *Leptospira*. Non-limiting examples of spirochetes include *Borrelia afzelii*, *Borrelia anserine*, *Borrelia burgdorferi* (such as *Borrelia burgdorferi* sensu lato), *Borrelia garinii*, *Borrelia hermsii*, *Borrelia recurrentis*, *Borrelia valaisiana*, *Borrelia vincentii*, *Brachyspira aalborgi*, *Brachyspira pilosicoli*, *Leptospira alexanderi*, *Leptospira biflexa*, *Leptospira broomii*, *Leptospira borgpetersenii*, *Leptospira fainei*, *Leptospira inadai*, *Leptospira interrogans*, *Leptospira kirschneri*, *Leptospira licerasiae*, *Leptospira meyeri*, *Leptospira noguchii*, *Leptospira santarosai*, *Leptospira weilii*, *Leptospira wolbachii*, *Leptospira kmetyi*, *Leptospira wolffii*, *Leptospira genomospecies* 1, *Leptospira genomospecies* 3, *Leptospira genomospecies* 4, *Leptospira genomospecies* 5 and *Treponema pallidum*.

The term "spirochete-supporting medium" refers to cell culture medium formulated to promote the growth of spirochetes in culture. Such media are known in the art. Non-limiting examples of spirochete-supporting medium include Barbour-Stoenner-Kelly (BSK) complete medium; Barbour-Stoenner-Kelly II (BSK II) complete medium; modified BSK medium (BSK-H) and MPM medium.

The term "subject" refers to a vertebrate or invertebrate animal. In some embodiments, the subject is an invertebrate, e.g., an arachnid or an insect, optionally an arachnid or insect that can bite a human or animal, such as a tick, a spider, a bed bug, a flea, a mosquito or a black fly. In some embodiments, the subject is a vertebrate animal, e.g., a mammal, such as a human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

Cell Culture Compositions and Methods

Over the past several decades, attempts to culture spirochetes, particularly from infected subjects, have been fraught with difficulties and plagued with inconsistent results. The present invention provides a spirochete culture technique with improved spirochete yield, allowing for more reliable diagnoses.

One aspect of the present invention provides a two-stage culture technique. The first stage is a short-term culture technique that allows for an in vitro expansion of spirochetes, while the second stage provides a long-term culture technique that provides stable growth of spirochetes over a period of weeks or months. Typically, spirochetes from the short-term culture are used to generate the long-term culture.

The short-term culture allows for an in vitro expansion of spirochetes. The short-term culture may be generated by inoculating a spirochete culture medium with a spirochete. The spirochete culture medium may comprise a spirochete-supporting medium, serum, a reducing agent and an antibiotic. Without being bound by theory, it is hypothesized that the serum in the spirochete culture medium provides the growth factors required for spirochete expansion and the reducing agent allows the spirochete to tolerate aerobic or partially aerobic environments, including microaerobic conditions.

Several spirochete-supporting medium are known in the art. Any suitable spirochete-supporting medium may be used in the spirochete culture medium. The spirochete-supporting medium may be a Barbour-Stoenner-Kelly (BSK) Culture Medium or a variant thereof, for example BSK medium, BSK-II medium, BSK-H medium, and BSK-S medium, preferably BSK-H medium. Alternatively, the spirochete-supporting media may be MPM or MKM.

Several cell culture sera are known in the art. Any suitable cell culture sera may be used in the spirochete culture medium. The serum may be selected from fetal bovine serum, fetal calf serum, horse serum, rabbit serum, chicken serum, caprine (goat) serum, human serum, ovine (sheep) serum, and porcine (pig) serum, e.g., rabbit serum. The concentration of serum can be between about 5% and about 20%, between about 10% and about 20%, between about 15% and 20%, between about 5% and about 15%, between about 10% and about 15%, between about 6% and about 15%, between about 7% and about 15%, between about 8% and about 15%, between about 9% and about 15%, between about 11% and about 15%, between about 12% and about 15%, between about 13% and about 15%, between about 14% and about 15%, between about 6% and about 12%, between about 7% and about 12%, between about 8% and about 12%, between about 9% and about 12%, between about 10% and about 12%, or between about 11% and about 12%. In some embodiments, the concentration of serum is about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20%, e.g., about 12%. Optionally, the concentration of serum is 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%, e.g., 12%.

Several cell culture reducing agents are known in the art. Any suitable cell culture reducing agent may be used in the spirochete culture medium, such as dithiothreitol (DTT), beta-mercaptoethanol, an iron-containing compound, amorphous ferrous sulfide, tris(2-carboxyethyl)phosphine, palladium chloride, sodium thioglycolate, cysteine×HCl, $Na_2S.9H_2O$, and sodium dithionite. Alternatively, the reducing agent is an enzyme such as a mono- and/or di-oxygenase, and/or succinate. In preferred embodiments, the reducing agent is DTT. The concentration of the reducing agent may be between about 0.05 μg/ml and about 1 μg/ml; between about 0.1 μg/ml and about 1 μg/ml; between about 0.1 μg/ml and about 0.9 μg/ml; between about 0.1 μg/ml and about 0.8 μg/ml; between about 0.1 μg/ml and about 0.7 μg/ml; between about 0.1 μg/ml and about 0.6 μg/ml; between about 0.1 μg/ml and about 0.5 μg/ml; between about 0.1 μg/ml and about 0.4 μg/ml; between about 0.1 μg/ml and about 0.3 μg/ml; or between about 0.1 μg/ml and about 0.2 μg/ml. In some embodiments, the concentration of the reducing agent is about 0.100 μg/ml; about 0.105 μg/ml; about 0.110 μg/ml; about 0.115 μg/ml; about 0.120 μg/ml; about 0.125 μg/ml; about 0.130 μg/ml; about 0.135 μg/ml; about 0.140 μg/ml; about 0.145 μg/ml; about 0.150 μg/ml; about 0.155 μg/ml; about 0.160 μg/ml; about 0.165 μg/ml; about 0.170 μg/ml; about 0.175 μg/ml; about 0.180 μg/ml; about 0.185 μg/ml; about 0.190 μg/ml; about 0.195 μg/ml; or about 0.200 μg/ml, e.g., 0.145 μg/ml. The concentration of the reducing agent may be 0.100 μg/ml; 0.105 μg/ml; 0.110 μg/ml; 0.115 μg/ml; 0.120 μg/ml; 0.125 μg/ml; 0.130 μg/ml; 0.135 μg/ml; 0.140 μg/ml; 0.145 μg/ml; 0.150 μg/ml; 0.155 μg/ml; 0.160 μg/ml; 0.165 μg/ml; 0.170 μg/ml; 0.175 μg/ml; 0.180 μg/ml; 0.185 μg/ml; 0.190 μg/ml; 0.195 μg/ml; or 0.200 μg/ml, e.g., 0.145 μg/ml. Alternatively, the concentration of the reducing agent may be between about 0.1 μg/ml and about 1000 μg/ml, about 0.1 μg/ml and about 500 μg/ml, about 0.1 μg/ml and about 250 μg/ml, about 0.1 μg/ml and about 100 μg/ml, between about 1 μg/ml and about 500 μg/ml, between about 1 μg/ml and about 250 μg/ml, between about 1 μg/ml and about 100 μg/ml, between about 10 μg/ml and about 250 μg/ml, between about 10 and about 100 μg/ml. between about 25 μg/ml and about 100 μg/ml, between about 50 μg/ml and about 100 μg/ml, between about 75 μg/ml and about 100 μg/ml or between about 90 μg/ml and about 100 μg/ml, such as between about 0.1 μg/ml and about 100 μg/ml. In some embodiments the concentration of the reducing agent is about 1 μg/ml, about 2 μg/ml, about 3 μg/ml, about 4 μg/ml, about 5 μg/ml, about 6 μg/ml, 7 μg/ml, about 8 μg/ml, about 9 μg/ml, about 10 μg/ml, about 20 μg/ml, about 30 μg/ml, about 40 μg/ml, about 50 μg/ml, about 60 μg/ml, about 70 μg/ml, about 80 μg/ml, about 90 μg/ml, about 100 μg/ml, about 125 μg/ml, about 150 μg/ml, about 175 μg/ml or about 200 μg/ml, e.g., about 100 μg/ml. In some embodiments the concentration of the reducing agent is 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 20 μg/ml, 30 μg/ml, 40 μg/ml, 50 μg/ml, 60 μg/ml, 70 μg/ml, 80 μg/ml, 90 μg/ml, 100 μg/ml, 125 μg/ml, 150 μg/ml, 175 μg/ml or 200 μg/ml, e.g., 100 μg/ml.

Several cell culture antibiotics are known in the art. In some embodiments, the antibiotic in the spirochete culture medium is an antibiotic to which spirochetes are resistant, such as rifampicin, which may be in the form of rifampicin antibiotic disc (BD Diagnostic). The concentration of the antibiotic may be about 0.5 μg/ml; about 1 μg/ml; about 1.5 μg/ml; about 2 μg/ml; about 2.5 μg/ml; about 3 μg/ml; about 3.5 μg/ml; about 4 μg/ml; about 4.5 μg/ml; about 5 μg/ml; about 5.5 μg/ml; about 6 μg/ml; about 6.5 μg/ml; about 7 μg/ml; about 7.5 μg/ml; about 8 μg/ml; about 8.5 μg/ml; about 9 μg/ml; about 9.5 μg/ml; about 10 μg/ml; about 15 μg/ml; about 20 μg/ml; about 25 μg/ml; about 30 μg/ml; about 35 μg/ml; about 40 μg/ml; about 45 μg/ml; about 50 μg/ml; about 55 μg/ml; about 60 μg/ml; about 65 μg/ml; about 70 μg/ml; about 75 μg/ml; about 80 μg/ml; about 85 μg/ml; about 90 μg/ml; about 95 μg/ml; or about 100 μg/ml, e.g., about 1 μg/ml. In some embodiments, the concentration of the antibiotic is 0.5 μg/ml; 1 μg/ml; 1.5 μg/ml; 2 μg/ml; 2.5 μg/ml; 3 μg/ml; 3.5 μg/ml; 4 μg/ml; 4.5 μg/ml; 5 μg/ml; 5.5 μg/ml; 6 μg/ml; 6.5 μg/ml; 7 μg/ml; 7.5 μg/ml; 8 μg/ml; 8.5 μg/ml; 9 μg/ml; 9.5 μg/ml; 10 μg/ml; 15 μg/ml; 20 μg/ml; 25 μg/ml; 30 μg/ml; 35 μg/ml; 40 μg/ml; 45 μg/ml; 50 μg/ml; 55 μg/ml; 60 μg/ml; 65 μg/ml; 70 μg/ml; 75 μg/ml; 80 μg/ml; 85 ng/ml; 90 μg/ml; 95 μg/ml; or 100 μg/ml, e.g., 1 μg/ml.

In a preferred embodiment, the spirochete culture medium comprises BSK-H supplemented with 12% rabbit serum, 0.145 μg/ml DTT and 1 μg rifampicin. In another preferred embodiment, the spirochete culture medium comprises BSK-H supplemented with 12% rabbit serum, 0.145 μg/ml DTT and a rifampicin antibiotic disc. In a further preferred embodiment, the spirochete culture medium comprises BSK-H supplemented with 12% rabbit serum, 100 μg/ml DTT and 1 μg rifampicin. In another preferred embodiment, the spirochete culture medium comprises BSK-H supplemented with 12% rabbit serum, 100 μg/ml DTT and a rifampicin antibiotic disc.

Using the culture method of the present invention, any spirochete can be cultured, including *Borrelia, Treponema, Brachyspira* and *Leptospira*, such as *Borrelia afzelii, Borrelia anserine, Borrelia burgdorferi* (such as *Borrelia burgdorferi* sensu lato), *Borrelia garinii, Borrelia hermsii, Borrelia recurrentis, Borrelia valaisiana, Borrelia vincentii, Brachyspira aalborgi, Brachyspira pilosicoli, Leptospira alexanderi, Leptospira biflexa, Leptospira broomii, Leptospira borgpetersenii, Leptospira fainei, Leptospira inadai, Leptospira interrogans, Leptospira kirschneri, Leptospira licerasiae, Leptospira meyeri, Leptospira noguchii, Leptospira santarosai, Leptospira weilii, Leptospira wolbachii, Leptospira kmetyi, Leptospira wolffii, Leptospira genomospecies* 1, *Leptospira genomospecies* 3, *Leptospira genomospecies* 4, *Leptospira genomospecies* 5 and *Treponema pallidum*. For example, the spirochete may be *Borrelia burgdorferi, Borrelia recurrentis, Treponema pallidum, Brachyspira pilosicoli* or *Brachyspira aalborgi*, preferably *Borrelia burgdorferi*, e.g., *Borrelia burgdorferi* sensu lato.

The source of the spirochete for short-term culture may be an established spirochete cell line, optionally a cell line that has been cryopreserved. In some embodiments, the established spirochete cell line is an established *Borrelia burgdorferi* cell line, such as the B31 strain, e.g., ATCC accession number 35210.

The source of the spirochete for short-term culture may be a subject suffering from a spirochete infection. The subject may be an invertebrate, e.g., an arachnid or an insect, optionally an arachnid or insect that can bite a human or animal, such as a tick, a spider, a bed bug, a flea, a mosquito or a black fly. Alternatively, the subject is a vertebrate animal, e.g., a mammal, such as a human. In some embodiments, the subject is a domestic or laboratory animal, such as a dog, a cat, a pig, a rabbit, a rat, a mouse, a gerbil, a hamster, a guinea pig, or a ferret. The subject may be a livestock animal, including an alpaca, a bison, a camel, cattle, a deer, a pig, a horse, a llama, a mule, a donkey, a sheep, a goat, a reindeer, or a yak.

Using the culture method of the present invention, spirochetes can be cultured from a sample of any fluid or tissue of an infected subject. The spirochete may be collected from samples of peripheral blood (serum), cerebrospinal and synovial fluids, or a biopsy of, for example, skin, bone marrow or joint lining, preferably a peripheral blood sample or a skin biopsy. In preferred embodiments, the spirochete is collected from a peripheral blood sample. Cultures may be prepared from samples collected from subjects who are seronegative.

The sample may be collected from a subject who is not actively undergoing antibiotic treatment. In some embodiments, the subject has not received antibiotics for at least four weeks prior to the sample collection. Optionally, the sample is collected in the morning. Alternatively, the sample is collected after noon.

The peripheral blood sample may be collected into a red VACUTAINER™ tube (no additive), a purple VACUTAINER™ tube (EDTA additive) or a 15 ml sterile Falcon tube containing about 5 ml of BSK-H medium. In some embodiments, the peripheral blood sample is collected into a red VACUTAINER™ tube (no additive). Alternatively, the peripheral blood sample is collected into a 15 ml sterile Falcon tube containing about 5 ml of BSK-H medium. The collected sample may be stored up to 24 hours prior to processing. The collected sample may be stored on ice or at room temperature. Optionally, the peripheral blood samples are incubated for about 2.5 to about 3 hours at room temperature prior to inoculation, which allows the serum to separate from blood cells without centrifugation. The peripheral blood samples may be centrifuged prior to inoculation, for example, at 1,000 rpm for 3 minutes at room temperature. Patient blood serum contains inhibitory factors that inhibit spirochete growth, so clinical samples should be diluted in a relatively large volume of fresh media to minimize the effects of such inhibitory factors.

The spirochete culture medium may be inoculated with serum from a peripheral blood sample. In some embodiments, about 0.05 ml, about 0.1 ml, about 0.15 ml, about 0.2 ml, about 0.25 ml, about 0.3 ml, about 0.35 ml, about 0.4 ml, about 0.45 ml or about 0.5 ml of serum is used to inoculate the short-term culture, e.g., about 0.2 ml or about 0.4 ml of serum. In some embodiments, 0.05 ml, 0.1 ml, 0.15 ml, 0.2 ml, 0.25 ml, 0.3 ml, 0.35 ml, 0.4 ml, 0.45 ml or 0.5 ml of serum is used to inoculate the short-term culture, e.g., 0.2 ml or 0.4 ml of serum.

Any type of short-term culture vessel may be used in the method of the invention. The short-term culture vessel is made of glass, polystyrene or polypropylene. Optionally, the culture vessel has a total volume less than about 5 ml, such as a total volume of about 5 ml, about 4.5 ml, about 4 ml, about 3.5 ml, about 3 ml, about 2.5 ml, about 2 ml, about 1.9 ml, about 1.8 ml, about 1.7 ml, about 1.6 ml, about 1.5 ml, about 1.4 ml, about 1.3 ml, about 1.2 ml, about 1.1 ml, about 1.0 ml, about 0.9 ml, about 0.8 ml, about 0.7 ml, about 0.6 ml, about 0.5 ml, about 0.4 ml, about 0.3 ml, about 0.2 ml, or about 0.1 ml, e.g., 2 ml. In some embodiments, the culture vessel has a total volume of 5 ml, 4.5 ml, 4 ml, 3.5 ml, 3 ml, 2.5 ml, 2 ml, 1.9 ml, 1.8 ml, 1.7 ml, 1.6 ml, 1.5 ml, 1.4 ml, 1.3 ml, 1.2 ml, 1.1 ml, 1.0 ml, 0.9 ml, 0.8 ml, 0.7 ml, 0.6 ml, 0.5 ml, 0.4 ml, 0.3 ml, 0.2 ml, or 0.1 ml, e.g., 2 ml. The short-term culture vessel may be a 2 ml sterile polystyrene vial, such as a 2 ml sterile cryovial. Alternatively, the short-term culture vessel may be a 15 ml sterile glass tube.

The short-term culture may be incubated at about 28-37° C., at about 28-36° C., at about 30-36° C., or at about 32-36° C., such as about 32° C., about 33° C., about 34° C., 35° C., or about 36° C., preferably at about 34° C. The short-term culture may be cultured in about 3-6% $CO_2$, such as about 3%, about 4%, about 5% $CO_2$ or about 6% $CO_2$, e.g., about 5% $CO_2$. The short-term culture may be incubated in a manner to allow adequate gas exchange for spirochete growth, such as incubation using the loose-cap method, including with the culture vessel left slightly open or incubation in a culture vessel with a vented lid.

The volume of the short-term culture may be about 50% to about 100% of the short-term culture vessel volume, including about 50%, about 55%, about 60%, about 65%, about 70%, about 75%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% of the short-term culture vessel volume, e.g., about 90% of the short-term culture vessel volume. In some embodiments, the volume of short-term culture is 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the culture vessel volume, e.g., 90% of the short-term culture vessel volume. Optionally, the volume of the short-term culture is about 1.8 ml, and the culture vessel volume is about 2.0 ml. Alternatively, the volume of the short-term culture is about 13.5 ml, and the culture vessel volume is about 15 ml.

The short-term culture may be incubated in about 80% to about 100% humidity, such as about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% humidity, preferably about 100%. In some embodiments, the short-term culture is incubated in 80%, 81%, 82%, 83%, 84%, 85%, 86%, 87%, 88%, 89%, 90%, 91%, 92%, 93%, 94%, 95%, 96%, 97%, 98%, 99% or 100% humidity, preferably 100% humidity.

The short-term culture is incubated in an anaerobic environment, including a microaerobic environment. The anaerobic or microaerobic environment may be obtained by varying the culture volume to culture vessel volume ratio or by using candle extinction in a sealed jar, the loose-cap method, flushing with inert gas, or the addition of an additional reducing agent, such as beta-mercaptoethanol, an iron-containing compound, amorphous ferrous sulfide, tris(2-carboxyethyl) phosphine, palladium chloride, sodium thioglycolate, cysteine×HCl, $Na_2S.9H_2O$, and sodium dithionite. In some embodiments, the additional reducing agent is an enzyme such as a mono- and/or di-oxygenase, and/or succinate.

The short-term culture can be incubated for less than 8 days, such as about 7 days, about 6 days, about 5 days, about 4 days, about 3 days, about 2 days or about 1 day. Optionally, the short-term culture is incubated for about 4-6 days, such as about 4 days, about 5 days or about 6 days.

After incubation, the short-term culture can be evaluated to detect the presence of spirochetes. The short-term culture may be examined for the presence of spirochetes using a dark-field microscope or a fluorescent microscope. A portion of the cells in the short-term culture can be stained with a dye, including a fluorescent dye, such as acridine orange. The acridine orange may be at pH 4.0 in acetate buffer. The stained cells may be visualized using a fluorescent microscope, e.g., after acridine orange staining. Cells from the short-term culture may be immunostained, e.g., with an antibody directed to a spirochete-specific marker, such as flagella, ospA and ospC. Detection of the spirochete-specific marker can identify the spirochete present in the short-term culture. Detection of the spirochete-specific marker may identify the spirochete present in the subject suffering from a spirochete infection. Typically, a minimum of $1\times10^5$ cells are required for immunostaining Optionally, DNA is extracted from the cells of the short-term culture, e.g., for PCR. The PCR may be performed with spirochete-specific primers, such as primers to amplify 16s rRNA, flagella, ospA or ospC encoding sequences or housekeeping genes. The spirochete-specific primers may identify the spirochete present in the short-term culture. The spirochete-specific primers may identify the spirochete present in the subject suffering from a spirochete infection. Typically, a minimum of $5\times10^6$ cells are required for DNA extraction. The short-term culture is used to inoculate one or more additional short-term cultures or one or more long-term cultures. Typically, a minimum of about $1\times10^5$ short-term culture cells are use to inoculate the long-term culture. Preferably, about $1\times10^5$ short-term culture cells are use to inoculate the long-term culture.

After about 8-12 days of short-term culture, the spirochetes irreversibly convert into different morphological forms. Without being bound by theory, it was hypothesized that long-term spirochete culture required an environment that mimicked the host environment in vivo because spirochetes are symbiotic organisms. Accordingly, spirochetes in long-term culture may be grown in the presence of a support matrix, such as collagen, fibronectin, laminin, peptidoglycan, elastin, and agarose, e.g., collagen, such as rat-tail collagen. The matrix may coat the culture vessel or may coat an insert in the culture vessel, such as a microscope slide, e.g., a collagen-coated slide.

The source of the spirochete for long-term culture may be an established spirochete cell line, optionally a spirochete cell line that has been cryopreserved. The established spirochete cell line may be an established *Borrelia burgdorferi* cell line, such as the B31 strain, e.g., ATCC accession number 35210. Alternatively, the source of the spirochete for long-term culture is a short-term culture, as described above. Typically, a minimum of about $1\times10^5$ short-term culture cells are used to inoculate the long-term culture. In some embodiments, about $1\times10^5$ short-term culture cells are used to inoculate the long-term culture. The long-term culture may be inoculated after the short-term culture has been incubated about 4-6 days, such as after the short-term culture has been incubated about 4 days, after the short-term culture has been incubated about 5 days, or after the short-term culture has been incubated about 6 days. Any suitable spirochete culture medium described above may be used in the long-term culture.

Any suitable culture vessel may be used in the long-term culture. The long-term culture vessel may contain one or more solid supports, preferably coated with a matrix, and a spirochete culture medium, as described above. The culture vessel may be a Coplin jar. The matrix may be collagen, fibronectin, laminin, peptidoglycan, elastin, or agarose, e.g., collagen. Optionally, the solid support is a wall of the culture vessel. Alternatively, the solid support may be separate from the culture vessel, such as a microscope slide, e.g., a collagen-coated slide, placed in the vessel. In some embodiments, the one or more solid supports are placed in the vessel, such that the vessel holds the one or more solid supports. The Coplin jar may contain 1, 2, 3, 4, 5, 6, 7, 8, 9 or 10 slides, e.g., 2 slides. The Coplin jar may have a total volume of 50 ml. Optionally, the Coplin jar contains 35 ml of spirochete culture medium.

In some embodiments, the long-term culture is incubated at about 28-37° C., at about 28-35° C., at about 30-35° C., or at about 33-35° C., such as about 33° C., about 34° C., or 35° C., e.g., 35° C. Preferably, the long-term culture is incubated at about 34° C. The long-term culture may be incubated in about 3-6% $CO_2$, such as about 3%, about 4%, about 5% $CO_2$, or about 6% $CO_2$, e.g., 5% $CO_2$.

The long-term culture may be incubated in about 80% to about 100% humidity, such as about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% humidity, preferably about 100% humidity. In some embodiments, the long-term culture is incubated in 80%, 81%, 82%, 83%, 84%, 85%, 86%, 87%, 88%, 89%, 90%, 91%, 92%, 93%, 94%, 95%, 96%, 97%, 98%, 99% or 100% humidity, preferably 100% humidity.

The long-term culture can be incubated for at least 3 months, for example 3 months, 4 months, 5 months, 6 months or longer. Optionally, the long-term culture is incubated for about one week, about two weeks, about three weeks, about four weeks, about five weeks, about six weeks, about seven weeks, about eight weeks, about nine weeks, about ten weeks, about eleven weeks, or about twelve weeks. The long-term culture may be monitored weekly, for example, the matrix-coated supports of the long-term culture may be monitored weekly for cell growth.

The matrix-coated supports, such as matrix-coated slides, may be used in assays to detect the presence of spirochetes in the long-term culture. The cells on the matrix-coated supports, such as matrix-coated slides, may be visualized on a dark-field microscope or a fluorescent microscope, for example, after dye staining. The dye may be acridine orange, e.g., acridine orange, pH 4.0 in acetate buffer, which may be visualized on a fluorescent microscope. The matrix-coated supports, such as matrix-coated slides, may be used in assays to identify the spirochete present in the long-term culture, for example, by immunostaining, such as with an antibody directed against a spirochete-specific marker (e.g., flagella, ospA, or ospC). The spirochete-specific marker may identify the spirochete present in the long-term culture, e.g., by identifying the specific spirochete species or subspecies. The spirochete-specific marker may identify the spirochete present in the subject suffering from a spirochete infection. The cells from the matrix-coated support, such as a matrix-coated slide, can be scraped in to medium, e.g., for DNA extraction and, optionally, PCR. The PCR may be performed with spirochete-specific primers (e.g., primers to amplify 16s rRNA, flagella, ospA, or ospC encoding sequences or housekeeping genes), which may identify the spirochete present in the long-term culture or in the subject suffering from a spirochete infection.

Method of Identifying a Spirochete

Spirochete infections have a variety of clinical manifestations, including, but not limited to, leptospirosis, Lyme disease, relapsing fever, syphilis, yaws, and intestinal spirochetosis. Each of these diseases is caused by infection with a different spirochete species or subspecies. The symptoms, complications and treatment methods for each of these diseases can vary. Many of these diseases present with variable symptoms, making clinical diagnosis difficult in the absence of a laboratory assay. A laboratory test that distinguishes between the various spirochete species will help treating physicians avoid complications and prescribe a suitable treatment.

Another aspect of the present invention provides a method of identifying a spirochete. The spirochete may be from an established cell line or from an uncharacterized cell culture. Alternatively, the spirochete may be from a subject possibly suffering from a spirochete infection. A sample from a subject suffering from a spirochete infection may be obtained by any of the sample collection methods described above. The spirochete from the established cell line, the uncharacterized cell culture or a sample from a subject suffering from a spirochete infection can be used to inoculate spirochete culture medium to establish a short-term spirochete culture, as described above. The spirochete may be identified after the short-term culture or the short-term culture may be used to generate a long-term culture, as described above, which can be used in an assay to identify the spirochete. Preferably, the short-term culture can be used both in an assay to identify the spirochete and to generate a long-term culture, which can be used in an assay to confirm the spirochete identity.

Several spirochete identity assays are known in the art. Any suitable assay may be used to identify the spirochete grown in either the short-term or the long term culture. In some embodiments, the assay is selected from an ELISA, a Western blot, an immunofluorescence assay, the Gunderson test, PCR, and an antigen capture test. In a preferred embodiment, the assay is an immunostaining assay, such as immunohistochemistry. The immunostaining assay may use antibodies directed to spirochete-specific markers (e.g., flagella, ospA, or ospC). The markers may be used to identify one species of spirochete from another. In another preferred embodiment, the assay is a PCR assay. The PCR assay may use spirochete-specific primers (e.g., primers to amplify 16s rRNA, flagella, ospA, or ospC encoding sequences), which may be used to identify one species of spirochete from another.

Any suitable spirochete may be identified by the method of the invention, including *Borrelia*, *Treponema*, *Brachyspira* and *Leptospira*, such as *Borrelia afzelii*, *Borrelia anserine*, *Borrelia burgdorferi* (such as *Borrelia burgdorferi* sensu lato), *Borrelia garinii*, *Borrelia hermsii*, *Borrelia recurrentis*, *Borrelia valaisiana*, *Borrelia vincentii*, *Brachyspira aalborgi*, *Brachyspira pilosicoli*, *Leptospira alexanderi*, *Leptospira biflexa*, *Leptospira broomii*, *Leptospira borgpetersenii*, *Leptospira fainei*, *Leptospira inadai*, *Leptospira interrogans*, *Leptospira kirschneri*, *Leptospira licerasiae*, *Leptospira meyeri*, *Leptospira noguchii*, *Leptospira santarosai*, *Leptospira weilii*, *Leptospira wolbachii*, *Leptospira kmetyi*, *Leptospira wolffii*, *Leptospira genomospecies* 1, *Leptospira genomospecies* 3, *Leptospira genomospecies* 4, *Leptospira genomospecies* 5 and *Treponema pallidum*. For example, the spirochetes *Borrelia burgdorferi*, *Borrelia recurrentis*, *Treponema pallidum*, *Brachyspira pilosicoli* and *Brachyspira aalborgi* can all be identified using this method. In particular embodiments, the spirochete is *Borrelia burgdorferi*, such as *Borrelia burgdorferi* sensu lato.

Method of Diagnosing a Spirochete Infection in a Subject

Spirochete infections present with variable symptoms, making clinical diagnosis difficult in the absence of a laboratory assay. Indeed, Lyme disease is routinely misdiagnosed, often being confused for the flu, Alzheimer's disease, Parkinson's disease ADD/ADhD, autism, juvenile arthritis, rheumatoid arthritis, reactive arthritis, infectious arthritis, osteoarthritis, fibromyalgia, Raynaud's Syndrome, chronic fatigue syndrome, interstitial cystis, gastroesophageal reflux disease, Fifth Disease, multiple sclerosis, scleroderma, lupus, early ALS, Crohn's disease, Ménières syndrome, Sjogren's syndrome, irritable bowel syndrome, colitis, prostatitis, psychiatric disorders, bipolar, depression, encephalitis, sleep disorders, or thyroid disease. A laboratory test that reliably identifies a spirochete infection will help treating physicians avoid complications and prescribe a suitable treatment. Culturing a spirochete from a subject is a direct test that definitively demonstrates the presence of an infection at the time the sample was taken from the subject.

Accordingly, another aspect of the present invention provides a method of diagnosing a spirochete infection in a subject. The subject may be any subject described above, and a sample from a subject suffering from a spirochete infection may be obtained by any of the sample collection methods described above. The spirochete obtained in a sample from a subject suffering from a spirochete infection can be used to inoculate spirochete culture medium to establish a short-term spirochete culture, as described above. Preferably, the presence of the spirochete may be detected after the short-term culture. Alternatively, the short-term culture may be used to generate a long-term culture, as described above, which can be used in an assay to detect the presence of the spirochete. Preferably, the short-term culture can be used both in an assay to detect the presence of the spirochete and to generate a long-term culture, which can be used in an assay to confirm the spirochete detection.

Several spirochete detection assays are known in the art. Any suitable assay may be used to detect spirochete growth in either the short-term or the long term culture. In some embodiments, the assay is selected from an ELISA, a Western blot, an immunofluorescence assay, the Gunderson test, PCR, and an antigen capture test. In a preferred embodiment, the assay is an immunostaining assay, such as immunohistochemistry. The immunostaining assay may use antibodies directed to spirochete-specific markers (e.g., flagella, ospA, or ospC). The markers may be used to detect the presence of one or more species of spirochete. In another preferred embodiment, the assay is a PCR assay. The PCR assay may use spirochete-specific primers (e.g., primers to amplify 16s rRNA, flagella, ospA, or ospC encoding sequences or housekeeping genes), which may be used to detect the presence of one or more species of spirochete.

Any suitable spirochete may be detected by the method of the invention, including *Borrelia, Treponema, Brachyspira* and *Leptospira*, such as *Borrelia afzelii, Borrelia anserine, Borrelia burgdorferi* (such as *Borrelia burgdorferi* sensu lato), *Borrelia garinii, Borrelia hermsii, Borrelia recurrentis, Borrelia valaisiana, Borrelia vincentii, Brachyspira aalborgi, Brachyspira pilosicoli, Leptospira alexanderi, Leptospira biflexa, Leptospira broomii, Leptospira borgpetersenii, Leptospira fainei, Leptospira inadai, Leptospira interrogans, Leptospira kirschneri, Leptospira licerasiae, Leptospira meyeri, Leptospira noguchii, Leptospira santarosai, Leptospira weilii, Leptospira wolbachii, Leptospira kmetyi, Leptospira wolffii, Leptospira genomospecies* 1, *Leptospira genomospecies* 3, *Leptospira genomospecies* 4, *Leptospira genomospecies* 5 and *Treponema pallidum*. For example, the spirochetes *Borrelia burgdorferi, Borrelia recurrentis, Treponema pallidum, Brachyspira pilosicoli* and *Brachyspira aalborgi* can all be detected using this method. In particular embodiments, the spirochete is *Borrelia burgdorferi*, such as *Borrelia burgdorferi* sensu lato.

Method of Identifying the Antibiotic Sensitivity of a Spirochete

Spirochete infections are typically difficult to treat and often relapse once treatment is stopped. The typical treatment for a spirochete infection is administration of antibiotics, including doxycycline, minocycline, amoxicillin, cefuroxime, and ceftriaxone. Although antibiotic treatment is successful in treating early stage infections and leads to a rapid improvement in a patient's condition, persistent symptoms develop after discontinuation of treatment, even when the antibiotic as been administered for a period of 2-4 weeks. Without being bound by theory, it has been hypothesized that the different morphological forms of spirochetes have different sensitivities to antibiotics. A laboratory test that reliably determines to which antibiotic treatment a spirochete is sensitive will help determine which antibiotic most effectively controls a given spirochete.

Accordingly, another aspect of the present invention provides a method of identifying the antibiotic sensitivity of a spirochete. The spirochete may be from an established cell line or from an uncharacterized cell culture. Alternatively, the spirochete may be from a subject suffering from a spirochete infection. A sample from a subject suffering from a spirochete infection may be obtained by any of the sample collection methods described above. The spirochete from the established cell line, the uncharacterized cell culture or a sample from a subject suffering from a spirochete infection can be used to inoculate spirochete culture medium to establish a short-term spirochete culture, as described above. The short-term culture can be used to either seed additional short-term cultures or long-term cultures. These additional short-term cultures or long-term cultures may include a test antibiotic. The test antibiotic may be present when the cultures are seeded or may be added subsequently. In a preferred embodiment, the test antibiotic is added to seeded culture when the spirochete concentration is about $1 \times 10^6$ cells/ml. The test cultures are typically incubated under the same conditions as the short-term cultures described above.

The spirochete can be incubated in the presence of the test antibiotic for up to three weeks and longer before cellular growth is scored. Preferably, the spirochete is incubated in the presence of the test antibiotic for about 12 hours, about 24 hours, about 36 hours, about 48 hours, about 60 hours, about 72 hours, about 84 hours, about 96 hours or any time period in between before cellular growth is scored. The spirochete, however, may be incubated in the presence of the test antibiotic for about one week, about two weeks, about three weeks, about four weeks, about five weeks, about six weeks, about seven weeks, about eight weeks, or any time period in between before cellular growth is scored. Spirochetes grown in the presence of the test antibiotic for more than a week should be grown in a long-term culture to avoid reversion to spheroplast or other forms. After such an incubation period, the spirochete may be cultured in medium lacking the test antibiotic to determine if spirochete growth will ensue after withdrawal of the antibiotic. Cultures may be maintained in culture lacking the test antibiotics for about 1 week, about 2 weeks, about 3 week, about 4 week, about 5 weeks or about 6 weeks, such as about 3 weeks.

Minimum inhibitory concentration (MIC) may be determined by evaluating the lowest concentration of the test antibiotic that will inhibit the visible growth of the spirochete. Methods of calculating and determining MIC are known in the art. MIC may be determined, for example, by determining the lowest concentration of the test antibiotic at which no spirochete movement is observed. MICs could be determined in the short-term culture of about half of the clinical samples tested. Minimum bactericidal concentration (MBC) may be determined by evaluating the lowest concentration of the test antibiotic that will kill the spirochete. Methods of calculating and determining MBC are known in the art. Typically, MBC calculations require determining if spirochete growth will ensue after withdrawal of the test antibiotic. Cellular growth may be scored by any suitable method. For example, cellular growth assays include directly counting the spirochete cells using a bacterial counting chamber and dark field microscopy. Alternatively, a bacterial viability assay, such as the LIVE/DEAD® BacLight™ Bacterial Viability Assay (Molecular Probes, Inc, Eugene, Oreg.), may be used to determine the ratio of live and dead spirochetes. The various morphological forms of the spirochete may also be scored. The sensitivity to the antibiotic may also be evaluated using an assay to detect cellular death of the spirochete.

Any suitable antibiotic may be used as the test antibiotic. The test antibiotic may be an aminoglycoside, an ansamycin, a carbacephem, a carbapenem, a cephalosporin, a glycopeptide, a lincosamide, a lipopeptide, a marcolide, a monobactam, a nitrofuran, a penicillin, a polypeptide antibiotic, a quinoline, a sulfanomide, or a tetracycline. In particular, the test antibiotic may be selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid.

Any suitable spirochete may be tested for antibiotic sensitivity by the method of the invention, including *Borrelia, Treponema, Brachyspira* and *Leptospira*, such as *Borrelia afzelii, Borrelia anserine, Borrelia burgdorferi* (such as *Borrelia burgdorferi* sensu lato), *Borrelia garinii, Borrelia hermsii, Borrelia recurrentis, Borrelia valaisiana, Borrelia vincentii, Brachyspira aalborgi, Brachyspira pilosicoli, Leptospira alexanderi, Leptospira biflexa, Leptospira broomii, Leptospira borgpetersenii, Leptospira fainei, Leptospira inadai, Leptospira interrogans, Leptospira kirschneri, Leptospira licerasiae, Leptospira meyeri, Leptospira noguchii, Leptospira santarosai, Leptospira weilii, Leptospira wolbachii, Leptospira kmetyi, Leptospira wolffii, Leptospira genomospecies* 1, *Leptospira genomospecies* 3, *Leptospira genomospecies* 4, *Leptospira genomospecies* 5 and *Treponema pallidum*. For example, the spirochetes *Borrelia burgdorferi, Borrelia recurrentis, Treponema pallidum, Brachyspira pilosicoli* and *Brachyspira aalborgi* can all be tested using this method. In particular embodiments, the spirochete is *Borrelia burgdorferi*, such as *Borrelia burgdorferi* sensu lato.

Method of Treating a Subject Suffering for a Spirochete Infection

As discussed above, spirochete infections are particularly difficult to treat and are prone to relapse once treatment is withdrawn. The typical treatment for a spirochete infection is administration of antibiotics, including doxycycline, minocycline, amoxicillin, cefuroxime, and ceftriaxone. Although antibiotic treatment is often successful in treating early stage infections and leads to a rapid improvement in a patient's condition, persistent symptoms develop after discontinuation of treatment, even when the antibiotic as been administered for a period of 2-4 weeks. Without being bound by theory, it has been hypothesized that the different morphological forms of spirochetes have different sensitivities to antibiotics. A laboratory test that reliably determines to which antibiotic treatment a spirochete is sensitive will help clinicians determine the proper treatment for the spirochete infection.

Accordingly, another aspect of the present invention provides a method of treating a subject suffering from a spirochete infection. The subject may be any subject described above, and a sample from a subject suffering from a spirochete infection may be obtained by any of the sample collection methods described above. The spirochete obtained in a sample from a subject suffering from a spirochete infection can be used to inoculate spirochete culture medium to establish a short-term spirochete culture, as described above. The short-term culture can be used to either seed additional short-term cultures or long-term cultures. These additional short-term cultures or long-term cultures may include a test antibiotic. The test antibiotic may be present when the cultures are seeded or may be added subsequently. In a preferred embodiment, the test antibiotic is added to seeded culture when the spirochete concentration is about $1 \times 10^6$ cells/ml. The test cultures are typically incubated under the same conditions as the short-term cultures described above.

The spirochete can be incubated in the presence of the test antibiotic for up to three weeks and longer before cellular growth is scored. Preferably, the spirochete is incubated in the presence of the test antibiotic for about 12 hours, about 24 hours, about 36 hours, about 48 hours, about 60 hours, about 72 hours, about 84 hours, about 96 hours or any time period in between before cellular growth is scored. The spirochete, however, may be incubated in the presence of the test antibiotic for about one week, about two weeks, about three weeks, about four weeks, about five weeks, about six weeks, about seven weeks, about eight weeks, or any time period in between before cellular growth is scored. Spirochetes grown in the presence of the test antibiotic for more than a week should be grown in a long-term culture to avoid reversion to spheroplast or other forms. After such an incubation period, the spirochete may be cultured in medium lacking the test antibiotic to determine if spirochete growth will ensue after withdrawal of the antibiotic. Cultures may be maintained in culture lacking the test antibiotics for about 1 week, about 2 weeks, about 3 week, about 4 week, about 5 weeks or about 6 weeks, such as about 3 weeks.

Minimum inhibitory concentration (MIC) may be determined by evaluating the lowest concentration of the test antibiotic that will inhibit the visible growth of the spirochete. Methods of calculating and determining MIC are known in the art. MIC may be determined, for example, by determining the lowest concentration of the test antibiotic at which no spirochete movement is observed. MICs could be determined in the short-term culture of about half of the clinical samples tested. Minimum bactericidal concentration (MBC) may be determined by evaluating the lowest concentration of the test antibiotic that will kill the spirochete. Methods of calculating and determining MBC are known in the art. Typically, MBC calculations require determining if spirochete growth will ensue after withdrawal of the test antibiotic. Cellular growth may be scored by any suitable method. For example, cellular growth assays include directly counting the spirochete cells using a bacterial counting chamber and dark field microscopy. Alternatively, a bacterial viability assay, such as the LIVE/DEAD® BacLight™ Bacterial Viability Assay (Molecular Probes, Inc, Eugene, Oreg.), may be used to determine the ratio of live and dead spirochetes. The various morphological forms of the spirochete may also be scored. The sensitivity to the antibiotic may also be evaluated using an assay to detect cellular death of the spirochete.

Any suitable antibiotic may be used as the test antibiotic. The test antibiotic may be an aminoglycoside, an ansamycin, a carbacephem, a carbapenem, a cephalosporin, a glycopeptide, a lincosamide, a lipopeptide, a marcolide, a monobactam, a nitrofuran, a penicillin, a polypeptide antibiotic, a quinoline, a sulfanomide, or a tetracycline. In particular, the test antibiotic may be selected from doxycycline, tigecycline, metronidazole, tinidazole, minocycline, amoxicillin, cefuroxime, ceftriaxone, azithromycin, aetronidazole, penicillin G, ceftriaxone and the combination of amoxicillin and probenecid.

Once the suitable antibiotic treatment for a patient's particular spirochete infection has been identified, a clinician can administer an effective amount of the test antibiotic to the subject suffering from the spirochete infection. The method may also determine the amount of antibiotic to administer and the duration of the antibiotic treatment. Such a determination may take into account the MIC and/or the MBC of the antibiotic for the spirochete.

Any suitable spirochete infection may be treated by the method of the invention, including *Borrelia*, *Treponema*, *Brachyspira* and *Leptospira*, such as *Borrelia afzelii*, *Borrelia anserine*, *Borrelia burgdorferi* (such as *Borrelia burgdorferi* sensu lato), *Borrelia garinii*, *Borrelia hermsii*, *Borrelia recurrentis*, *Borrelia valaisiana*, *Borrelia vincentii*, *Brachyspira aalborgi*, *Brachyspira pilosicoli*, *Leptospira alexanderi*, *Leptospira biflexa*, *Leptospira broomii*, *Leptospira borgpetersenii*, *Leptospira fainei*, *Leptospira inadai*, *Leptospira interrogans*, *Leptospira kirschneri*, *Leptospira licerasiae*, *Leptospira meyeri*, *Leptospira noguchii*, *Leptospira santarosai*, *Leptospira weilii*, *Leptospira wolbachii*, *Leptospira kmetyi*, *Leptospira wolffii*, *Leptospira genomospecies* 1, *Leptospira genomospecies* 3, *Leptospira genomospecies* 4, *Leptospira genomospecies* 5 and *Treponema pallidum*. For example, the spirochetes *Borrelia burgdorferi*, *Borrelia recurrentis*, *Treponema pallidum*, *Brachyspira pilosicoli* and *Brachyspira aalborgi* can all be tested using this method. In particular embodiments, the spirochete is *Borrelia burgdorferi*, such as *Borrelia burgdorferi* sensu lato.

EXAMPLES

In order that this invention be more fully understood, the following examples are set forth. These examples are for the purpose of illustration only and are not to be construed as limiting the scope of the invention in any way.

Example 1

Cell Culture Composition

Spirochetes, including *Borrelia*, such as *Borrelia burgdorferi* and *Borrelia recurrentis*, were grown in the various published spirochete-supporting media. These species were selected as representative of the *Borrelia, Treponema, Brachyspira* and *Leptospira* genera, and the results reported below suggest that the methods described herein may be used for these genera. Specifically, $5\times10^6$ spirochetes were grown in 12 ml sterile glass tubes containing 10 ml spirochete-supporting medium. The various spirochete-supporting media included Barbour-Stoenner-Kelly-H medium (BSK-H medium) with 6% rabbit serum (available commercially from Sigma Chemical Co., St. Louis, Mo.); BSK-II medium. (described in Barbour, A. G. 1983. *Yale J. Biol. Med.* 57:521-525); modified Kelly medium (MKP medium, described in Preac-Mursic, et al. 1986. *Zentbl. Bakteriol. Mikrobiol. Hyg. Ser*. A 263:112-118); MPM medium (described in Phillips S E, et al., 1998, *Infection,* 26(6):364-7); BSK modified medium (described in Rodríguez I, et al., 2007, *Mem Inst Oswaldo Cruz, Rio de Janeiro,* 102(8): 999-1002); solid BSK based medium (described in De Martino S J, et al. 2006, *Res Microbiol,* 157(8):726-729); and PMR agar medium (described in V. Preac-Mursic, et al., 1991, *European Journal of Clinical Microbiology Infectious diseases* 10:1076-1079). The spirochetes were incubated in a $CO_2$ incubator at 34° C. with 5% $CO_2$ and 100% humidity for 6 days, at which time spirochete growth was evaluated by dark-field microscopy and a standard acridine orange staining protocol. Of the various spirochete-supporting media tested, both BSK-H medium and MPM supported the most significant spirochete growth, with BSK-H medium yielding significantly more spirochete growth (FIG. 1).

The original BSK-H medium was modified to obtain improved spirochete growth conditions. Serum concentration, magnesium concentration, and different types and concentrations of antibiotics were all tested. To determine the effect of serum concentration on spirochete growth, *Borrelia burgdorferi* were cultured in BSK-H medium with 6%, 12% or 20% rabbit serum. The spirochetes were incubated in a $CO_2$ incubator at 32° C. with 5% $CO_2$ and 100% humidity for 6 days, at which time spirochete growth was evaluated by dark-field microscopy. While all three serum concentrations supported spirochete growth, culturing spirochetes in 12% rabbit serum yielded the highest number of spirochete. See, FIG. 2A, p=0.008.

To determine the effect of magnesium concentration on spirochete growth, *Borrelia burgdorferi* were cultured in BSK-H medium with 6% rabbit serum and either $7.5\times10^{-2}$ M $MgCl_2$, or $7.5\times10^{-3}$ M $MgCl_2$. The spirochetes were incubated in a $CO_2$ incubator at 32° C. with 5% $CO_2$ and 100% humidity for 6 days, at which time spirochete growth was evaluated by dark-field microscopy. No significant differences in spirochete growth were observed for the two different magnesium concentrations (data not shown).

The effect of the addition of a reducing agent, such as DTT, to the culture media was also evaluated. To determine the effect of DTT concentration on spirochete growth, *Borrelia burgdorferi* were cultured in BSK-H medium with 6%, 12%, and 20% rabbit serum and either 0.145 μg/ml DTT or 100 μg/ml DTT. The spirochetes were incubated in a $CO_2$ incubator at 34° C. with 5% $CO_2$ and 100% humidity for 6 days, at which time spirochete growth was evaluated by dark-field microscopy. Including DTT in the culture medium increased spirochete yields. See, FIG. 2B. BSK-H with 12% rabbit serum with DTT yielded the most spirochetes, with 100 μg/ml DTT yielding twice as many spirochetes as 0.145 μg/ml DTT. See, FIG. 2B, p=0.0002.

To determine the effect of antibiotic concentration on spirochete growth, *Borrelia burgdorferi* were cultured in BSK-H medium containing 12% rabbit serum, 100 μg/ml DTT and one of the following antibiotics: 0.5 μg/ml rifampicin, 50 μg/ml rifampicin, a 5 μg/ml rifampicin disc (resulting in final concentration of 0.4 μg/ml), 50 μg/ml phosphomycin, 100 μg/ml phosphomycin, or the combination of 50 μg/ml rifampicin and 50 μg/ml phosphomycin. The spirochetes were incubated in a $CO_2$ incubator at 34° C. with 5% $CO_2$ and 100% humidity for 6 days, at which time spirochete growth was evaluated by dark-field microscopy. Culturing spirochetes in phosphomycin significantly decreased spirochete yield, while rifampicin did not affect spirochete yield significantly at low concentration (0.4-0.5 μg/ml). See, FIG. 2C. High rifampicin concentrations (e.g., 50 μg/ml), however, decreased spirochete yield (FIG. 2C). Lower concentrations of phosphomycin (e.g., 10 and 50 μg/ml) also significantly decreased spirochete yields (data not shown). Accordingly, for spirochetes obtained from patient samples, lower rifampicin concentrations (e.g., 0.5 μg/ml or a 5 μg/ml disc) are preferred.

Based on the studies above, a preferred spirochete growth medium comprised BSK-H medium (available from Sigma, St. Louis, Mo.) supplemented with 12% (total) rabbit serum, 100 μg/ml DTT (Sigma) and 1 μg/ml rifampicin (Sigma). Another preferred spirochete growth medium comprised BSK-H medium (available from Sigma, St. Louis, Mo.) supplemented with 12% (total) rabbit serum, 0.145 μg/ml DTT (Sigma) and 1 μg/ml rifampicin (Sigma). Alternatively, a rifampicin antibiotic disc (BD Diagnostics) could be used without affecting culture yield.

Example 2

Cell Culture Conditions

Spirochete cultures are typically grown in anaerobic conditions. To determine the effect of environmental oxygen on spirochete growth, *Borrelia burgdorferi* B31 cells were cultured on solid BSK-H medium and incubated in anaerobic and microaerobic conditions. Environmental oxygen levels were regulated using a BD BBL GASPAK™ environmental system. After 20 days, the surfaces of the BSK-H plates were evaluated for spirochete growth. The anaerobic environment did not yield any visible *Borrelia* growth, while the microaerobic environment yielded visible colonies on the surface of the culture plates. Colonies from the microaerobic culture plate were picked with a sterile loop, and live spirochetes were observed by dark-field microscopy (FIG. 3).

In published studies, researchers typically cultured *Borrelia* species in 5-15 ml glass tubes with tightly closed lids to prevent any gas exchange and maintain an anaerobic environment. To determine the effect of culture tube composition and gas exchange on spirochete growth, *Borrelia burgdorferi* B31 cells were cultured in BSK-H medium, 12% rabbit serum, 100 μg/ml DTT and 1 μg/ml rifampicin in glass tubes, polystyrene tubes and polypropylene tubes. The B31 cells were also cultured in tubes with closed lids and tubs with loose lids, which allowed for gas exchange with the environment. The cultures were incubated in a $CO_2$ incubator at 34° C. with 5% $CO_2$ and 100% humidity for 6 days, at which time spirochete growth was evaluated by dark-field microscopy. As shown in Table 1, no significant difference was observed in spirochete growth based on the culture vessel composition. Further, preventing gas exchange by using a closed-lid tube reduced spirochete growth significantly. Allowing gas exchange with a loose-lid tube promoted spirochete growth, likely due to the spirochete's preference for microaerobic conditions. A BD BBL GASPAK™ environmental system was used to more precisely control oxygen and $CO_2$ concentrations, but the GASPAK™ environmental system did not improve the spirochete yield over the preferred growth culture conditions (data not shown). Without being bound by theory, the addition of a reducing agent, such as DTT, is believed to have helped the cells to survive in the microaerobic environment. Further, in the absence of DTT, only alternative morphological forms of *Borrelia* were present in culture.

To determine the effect of culture vessel volume on spirochete growth, *Borrelia burgdorferi* B31 cells were cultured in BSK-H medium, 12% rabbit serum, 100 µg/ml DTT and 1 µg/ml rifampicin in 2 ml, 12 ml, 15 ml, and 50 ml polystyrene and glass tubes and 50 ml Coplin jars. The cultures were incubated in a $CO_2$ incubator at 34° C. with 5% $CO_2$ and 100% humidity for 6 days, at which time spirochete growth was evaluated by dark-field microscopy. As shown in Table 1, spirochetes preferentially grew in 2 ml polystyrene culture vessels, 15 ml glass tubes and 50 ml Coplin Jars. It was noted for clinical samples, however, that some cultures would only grow in 2 ml polystyrene tubes, while other cultures would only grow in 15 ml glass tubes. Accordingly, a preferred method of culturing spirochetes obtained from patient samples should include growth in both 2 ml polystyrene tubes and 15 ml glass tubes (see, e.g., Table 4, infra).

To determine if the ratio of culture media volume to culture vessel volume affected spirochete growth, *Borrelia burgdorferi* B31 cells were cultured in BSK-H medium, 12% rabbit serum, 0.145 µg/ml DTT and 1 µg/ml rifampicin in 2 ml loose-cap polystyrene tubes comprising 50% (1.0 ml), 60% (1.2 ml), 70% (1.4 ml), 80% (1.6 ml) and 90% (1.8 ml) culture media by volume. The cultures were incubated in a $CO_2$ incubator at 32° C. with 5% $CO_2$ and 100% humidity for 6 days, at which time spirochete growth was evaluated by dark-field microscopy. As shown in Table 1, spirochetes preferentially grew in culture vessels comprising 90% (1.8 ml) culture media. Without being bound by theory, the high ratio of culture media is believed to help maintain a microaerobic environment in the culture media by limiting gas exchange with the culture incubator.

To determine preferred temperature for spirochete growth, *Borrelia burgdorferi* B31 cells were cultured in BSK-H medium, 12% rabbit serum, 0.145 µg/ml DTT and 1 µg/ml rifampicin in 2 ml loose-cap polystyrene tubes comprising 90% (1.8 ml) culture media by volume. The cultures were incubated in a $CO_2$ incubator with 5% $CO_2$ and 100% humidity at 28° C., 30° C., 32° C., and 34° C. for 6 days, at which time spirochete growth was evaluated by dark-field microscopy. As shown in Table 1, spirochetes preferentially grew at 32° C. and 34° C.

TABLE 1

| Culture Conditions | Spirochete Yield | Culture Conditions | Spirochete Yield |
|---|---|---|---|
| Culture Vessel | | | |
| Glass Tubes-closed lid | ++ | Glass Tubes-loose lid | +++ |
| Polystyrene Tubes-closed lid | ++ | Polystyrene Tubes-Loose lid | +++ |
| Polypropylene Tubes-closed lid | ++ | Polypropylene Tubes-loose lid | +++ |
| Vessel Volume | | | |
| 2 ml Tubes | +++ | 50 ml Tubes | +++ |
| 12 ml Tubes | ++ | 50 ml Coplin Jar | +++ |
| 15 ml Tubes | ++ | | |
| Media Volume | | | |
| 50% culture vessel volume | ++ | 80% culture vessel volume | ++++ |
| 60% culture vessel volume | ++ | 90% culture vessel volume | +++++ |
| 70% culture vessel volume | ++ | | |
| Incubation Temperature | | | |
| 28° C. Incubation | ++ | 32° C. Incubation | ++++ |
| 30° C. Incubation | ++ | 34° C. Incubation | ++++ |

The in vitro studies described above were confirmed using cultures from 50 seropositive Lyme disease patients. Cultures from 27 of the 50 patients were positive for *Borrelia* by 6 days, as determined using a fluorescently labeled polyclonal anti-*Borrelia burgdorferi* antibody. Of the 27 positive cultures, 5 were positive in both culture environments, while 17 cultures were positive in the 15 ml glass tube only, and 5 samples grew exclusively in the 2 ml tube system.

Based on the studies above, a preferred spirochete culture condition includes growth in 15 ml glass tubes with 90% (13 ml) culture media by volume in a $CO_2$ incubator at 34° C. with 5% $CO_2$ and 100% humidity. However, because some clinical samples grew exclusively in the 2 ml tube system, using both systems during the short-term culture phase may increase the probability of a successful culture and the ultimate reliability of diagnostic results.

Example 3

Long Term Spirochete Culture

Figure 4:
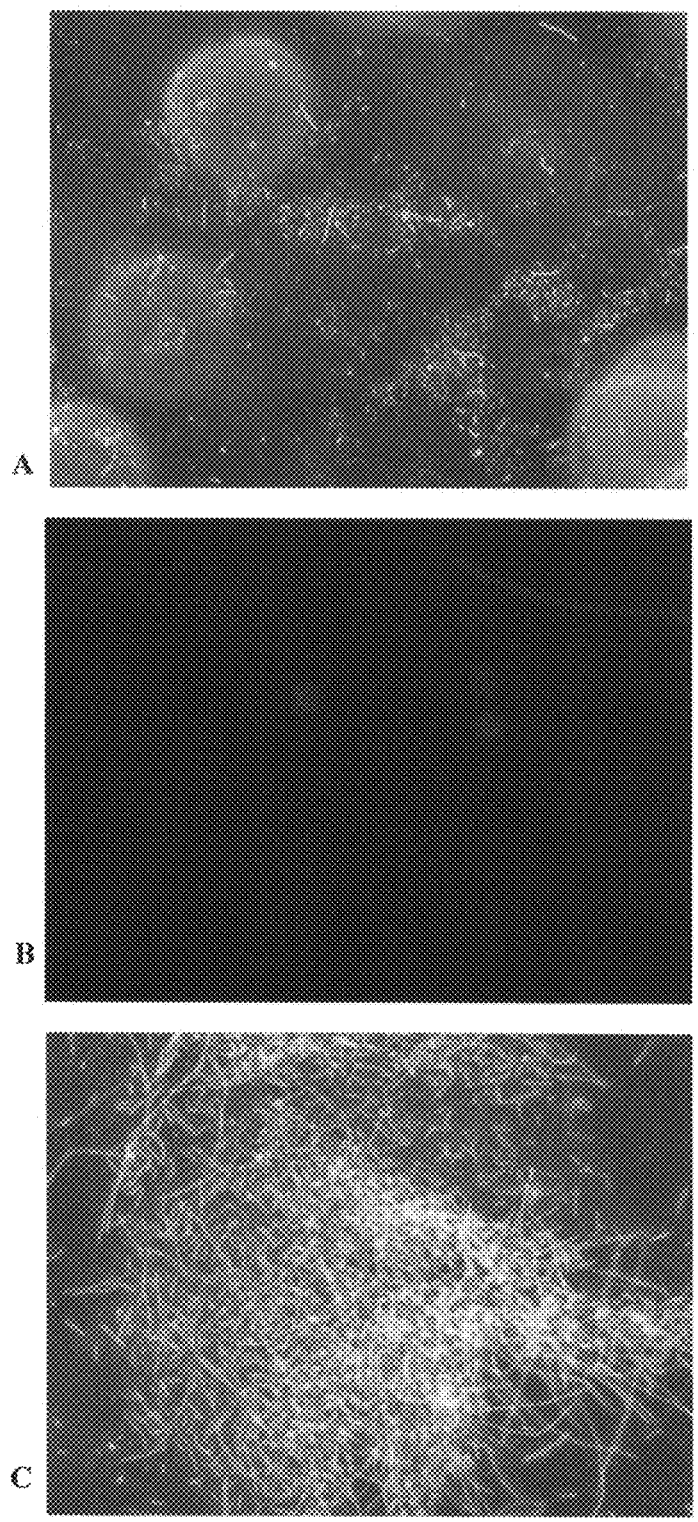
FIG. 4 shows serum cultures from the blood of a CDC positive Lyme disease patient containing bacterial cells with different morphologies after 6 days (panel A) or 12 days (panel B) of incubation in BSK-H medium with 12% rabbit serum and 100 µg/ml DTT at 34° C. with 5% $CO_2$ and 100% humidity in $CO_2$ incubator. At day 6 of the culture, the bacterial cells maintained spirochetal morphology (Panel A), but after 12 days of culture, the spirochetes reverted to spheroplast cells (panel B). The spheroplasts were stained positive with fluorescence labeled polyclonal antibody specific for *Borrelia burgdorferi* (Panel B, green label). The spheroplast cells were cultured for an additional 3 months; neither growth nor reconversion to spirochete was observed. Transferring approximately $1 \times 10^5$ cells from the six-day culture with spirochetal morphology to a 50 ml Coplin jar (Fisher) containing two collagen-coated slides (BD Scientific) and 35 ml of BSK-H medium with 12% rabbit serum and 100 µg/ml DTT with rifampicin antibiotic discs (BD Diagnostics), however, yielded significant numbers of spirochetal colonies on the collagen-coated slides after 6 weeks (panel C). Magnification 400×.

As described in Example 2, 50 clinical cultures were grown using the short-term conditions. The cells maintained their spirochetal structure through 6 days of culture. See, e.g., FIG. 4A. After about 10-12 days, the spirochetes in each and every culture converted into different morphological forms and all attempts to revert them back to spirochete form failed. See, e.g., FIG. 4B. Attempts to revert the spirochetes tested the various published spirochete-supporting medium, the amount of medium, culture temperature, $CO_2$ concentration, culture tube size, and culture tube composition (e.g., glass and polystyrene), as described in Examples 1 and 2. Most frequently, spirochetes converted into spheroplast form, as well as different round body forms (granules, cysts).

Accordingly, the culture conditions were changed prior to the morphological conversion in an attempt to prevent the conversion. Because *Borrelia* is a symbiotic organism, an environment mimicking the host system was used. Collagen, fibronectin, laminin, peptidoglycan, elastin, agarose were tested to find the best support matrix for long-term spirochete growth. As shown in Table 2, the collagen rat-tail 1 matrix most efficiently prevented the spirochete morphological conversion of the matrices tested. Therefore, all short-term cultures were converted into long-term cultures at day 6. Approximately $1 \times 10^5$ spirochete cells were added to a 50 ml Coplin jar (Fisher) containing two collagen-coated slides (BD Scientific) and 35 ml of BSK-H medium, 12% rabbit serum, 100 µg/ml DTT with rifampicin antibiotic discs (BD Diagnostics). Significant numbers of spirochetal colonies were identified after 6 weeks on the collagen-coated slides. See, e.g., FIG. 4C. The collagen-coated slides can be directly used for immunohistochemical analyses (see, e.g., Example 8, infra). Alternatively, PCR can be performed on spirochete cells scraped from the collagen-coated slides. Spirochetes from patient sera were also cultured directly in the Coplin jars with collagen slides, modified BSK-H medium and rifampicin (without the initial short-term culture conditions described in Example 2), but none of the inoculates resulted in a positive culture (data not shown).

TABLE 2

| Culture Conditions | Spirochete Yield |
|---|---|
| Collagen coated slides (Commercial) | +++++ |
| Rat tail collagen I coated slides | +++++ |
| Rat tail collagen II coated slides | ++++ |
| Matrigel coated slides | ++ |
| NanoCollagen coated Slides | ++++ |
| Fibronectin coated slides | +++ |
| Laminin coated slides | +++ |
| Peptidoglycan coated slides | +++ |
| Elastin coated slides | +++ |
| Agarose coated slides | + |
| Rat tail collagen I coated Mica disc | + |
| Collagen coated nanobeads | ++ |

Example 4

Obtaining a Spirochete Sample from a Subject

Peripheral blood samples from patients suffering from Lyme disease were collected into a red VACUTAINER™ tube (no additive), a purple VACUTAINER™ tube (with EDTA) or into a 15 ml sterile Falcon tube containing 5 ml BSK-H complete medium (Sigma). Blood samples from 50 seropositive Lyme disease patients were shipped overnight at room temperature in a Styrofoam box. The blood samples were incubated at room temperature for 2-3 hours to allow the blood to separate into separate fractions. Approximately 0.2-0.4 ml of the serum fraction was used to inoculate the culture medium described in Examples 1 and 2. The inoculated medium was cultured by the two-step (short-term and long-term) method described in Example 3. Collectively, 27 positive cultures were obtained. Blood samples collected into 15 ml Falcon tubes containing 5 ml BSK-H complete medium provided 24 of 27 positive cultures and yielded the highest number of spirochete cells. Blood samples collected into red VACUTAINER™ tubes (no additive) provided 11 of 27 positive cultures and yielded about half the number of spirochete cells. See, e.g., Table 3. Only 3 positive cultures grew exclusively in red VACUTAINER™ tubes, while 8 positive cultures grew in both 15 ml Falcon tubes and red VACUTAINER™ tubes. Blood samples collected into purple VACUTAINER™ tubes (containing EDTA) yielded spirochete cells in only a single culture inoculated, and the number of spirochete cells after 6 days of culture was never more than 25% of the number of spirochete cells yielded by the samples collected into Falcon tubes with BSK-H medium. See, e.g., Table 3. Accordingly, a preferred method of culturing spirochetes obtained from patient samples may include growth from both 15 ml Falcon tubes and red VACUTAINER™ tubes (see, e.g., Table 5, infra).

TABLE 3

| Patient # | Serum culture from the blood collected in 15 ml Falcon tube with 5 ml BSK-H | Serum culture from the blood collected in red cap VACUTAINER™ tube | Serum culture from the blood collected in purple cap VACUTAINER™ tube |
|---|---|---|---|
| 42 | $1 \times 10^7$ cells/ml | $4 \times 10^6$ cells/ml | $2.2 \times 10^6$ cells/ml |
| 43 | $6.2 \times 10^6$ cells/ml | $3.5 \times 10^6$ cells/ml | No cells observed |

In addition to the collection tube, other factors were found to affect spirochete yield in samples from patients. Low culture yields and inaccurate diagnostic test results were observed in patients who had been treated with antibiotics up to four weeks prior to the blood draw. For example, initial cultures from Patient 13 yielded significant numbers of cells in both short-term and long-term cultures (see, FIG. 9B). After a month of antibiotic treatment, culture samples from the same seropositive Patient 13 yielded no spirochete growth. Similar results were observed in other seropositive patients who were being treated with antibiotics at the time of blood collection. Accordingly, antibiotic therapeutic treatment may interfere with subsequent attempts to culture spirochetes and to diagnose spirochete infections. Also, the time of day at which the blood was drawn affected culture yield and diagnostic test results. Afternoon blood draws yielded higher spirochete numbers and more reliable diagnostic results than morning blood draws (data not shown). The reliability of diagnostic test results from the morning blood draws was not affected by the fed/fasted state of the patient.

Example 5

Two-Step Culture Method

Based on the results from Examples 1-4, a preferred method for culturing spirochetes from patients is as follows.
(1) Three blood samples (totaling ~30 ml/patient) were collected after 12 noon in the following samples: (a) one approximately 9.5-10 ml peripheral blood sample collected into a 15 ml sterile polypropylene tube containing 5 ml BSK-H and (b) two approximately 9.5-10 ml peripheral blood samples each collected into a 10 ml red cap (no additive) VACUTAINER™ tube.
(2) The blood samples were shipped overnight at room temperature in a Styrofoam box.
(3) The blood samples were incubated at room temperature for 2.5-3 hours to separate the serum from the blood cells.
(4) The blood samples were additional centrifuged at 200 g for 3 minutes at room temperature to further separate the serum.
(5) Eight short-term cultures were set up in 2 ml and 15 ml as shown in Table 4.

TABLE 4

| No | Tube volume | Culture medium | Serum/Plasma | Total volume (ml) |
|---|---|---|---|---|
| #1-2 | 2 ml polystyrene | 1.4 ml of BSK-H* + 0.5 mg/ml rifampicin | 0.4 ml serum from the tube containing blood in 5 ml BSK-H medium | 1.8 |
| #3-4 | 2 ml polystyrene | 1.6 ml of BSK-H* + 0.5 mg/ml rifampicin | 0.2 ml serum from red cap tube | 1.8 |

TABLE 4-continued

| No | Tube volume | Culture medium | Serum/Plasma | Total volume (ml) |
|---|---|---|---|---|
| #5-6 | 15 ml glass | 11.0 ml of BSK-H* + rifampicin disc | 2.0 ml serum from the tube containing blood in 5 ml BSK-H medium | 13.0 |
| #7-8 | 15 ml glass | 11.5 ml of BSK-H* + rifampicin disc | 1.5 ml serum from red cap tube | 13.0 |

*= BSK-H with 12% rabbit serum + 100 µg/ml DTT as a final concentration (6) The samples were incubated in an incubator at 34° C. with 5% $CO_2$ and 100% humidity. The lids of the vials were lightly closed to continue to allow gas exchange.

(7) After six days in culture, the samples from tubes 1, 3, 5 and 7 were centrifuged at 9,600 g for 10 minutes at room temperature. The supernatant was discarded and the pellet was resuspended 1 ml PBS pH 7.4. The centrifugation step was repeated, and the pellet was resuspended in 75 microliters PBS pH 7.4. The resuspended pellet was used for immunohistochemical and PCR studies.

Figure 5:
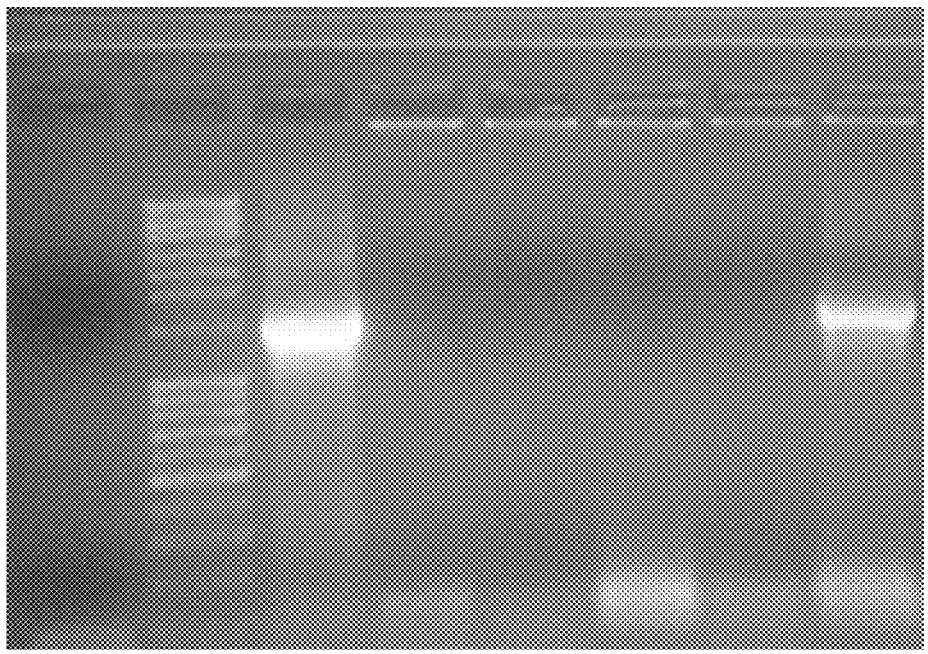
FIG. 5 shows polymerase chain reaction (PCR) analyses of the DNA expression of *Borrelia burgdorferi* DNA extracted from control strain and patient culture: PCR was performed using primers for 16s rDNA. The expected band at 1500 bp was clearly visualized in lanes 3 and 8. Lane 2 had 1 Kb plus DNA ladder. Lane 1 had negative control. Lanes 3 to 8 had the PCR amplified samples from cultures. Lane 3 had a positive control DNA (B31) and lanes 4 to 8 had DNA from a patient culture.

(8) 10 microliters of each resuspended culture was stained with 100 µg/ml acridine orange stain at pH 4.0 in acetate buffer. The presence of spirochetes and potential contaminants was evaluated by fluorescent microscopy, and cell number was estimated by counting the acridine orange stained spirochetal cells. If sufficient cells remained in excess, approximately $1 \times 10^5$ cells were used for spirochete-specific immunostaining, and the remaining culture was used for PCR confirmation with spirochete-specific primers (see, e.g., FIG. 5).

(9) The cultures in tubes 2, 4, 6 and 8 were combined and supplemented with BSK-H* media for a total volume of 40 ml, which was added to a 50 ml Coplin jar that contained two collagen-coated slides. The Coplin jars were incubated in an incubator at 34° C. with 5% $CO_2$ and 100% humidity for 8-16 weeks. After 8 weeks, one of the collagen-coated slides was removed from the long-term culture, washed 3× with PBS pH 7.4 and used for DNA extraction and PCR analyses using spirochete-specific markers. The cells on the remaining collagen-coated slide were scraped into the media of the long-term culture. Twenty ml were removed from the long-term culture and centrifuged at 9,600 g for 10 minutes at room temperature. The resulting pellet was resuspended in 1 ml PBS pH 7.4. The centrifugation step was repeated, and the pellet was resuspended in 50 microliters PBS pH 7.4 and used for immunohistochemical analyses. Additionally, two new collagen-coated slides and twenty ml of fresh BSK-H media were added to the remaining long-term culture in the coplin jar, which was incubated for an additional eight weeks. After the additional eight weeks, immunohistochemical and PCR analyses were performed as described.

Example 6

Culture Method Specificity

Figure 6:
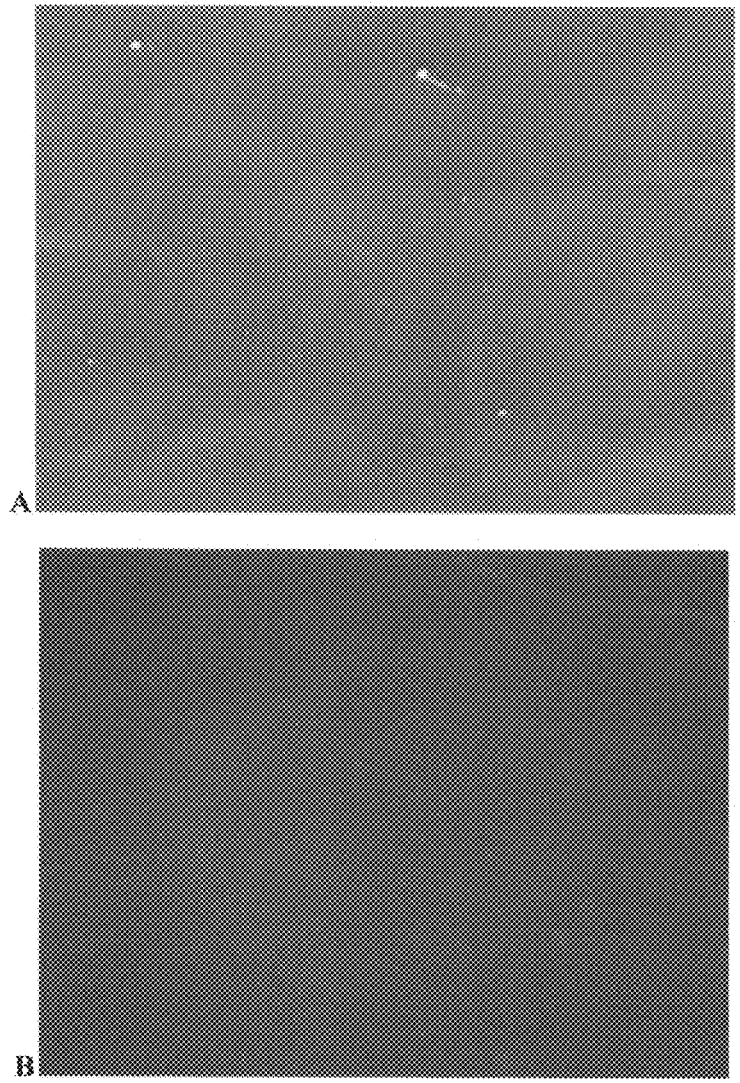
FIG. 6 shows blood samples from healthy individuals (i.e. negative control) cultured in modified BSK-H medium: Panel A shows absence of any spirochete bacteria under dark-field microscope in a short term culture, and Panel B is the same culture stained with acridine orange and visualized under fluorescent microscope. Magnification: 400×.

Peripheral blood samples (30 ml) were collected from 45 healthy donors in red cap VACUTAINER™ tubes and 15 ml polypropylene tubes as described in Example 5. The samples were prepared and cultured as described in Example 5. No spirochetal organisms were identified in any short-term or long-term cultures from any of the healthy donors. While most control cultures yielded some small pleomorphic organisms, these organisms did not have spirochetal forms, did not stain with acridine orange, and did not grow in the culture system. See, FIG. 6.

Example 7

Confirming the Culture Method

Figure 7:
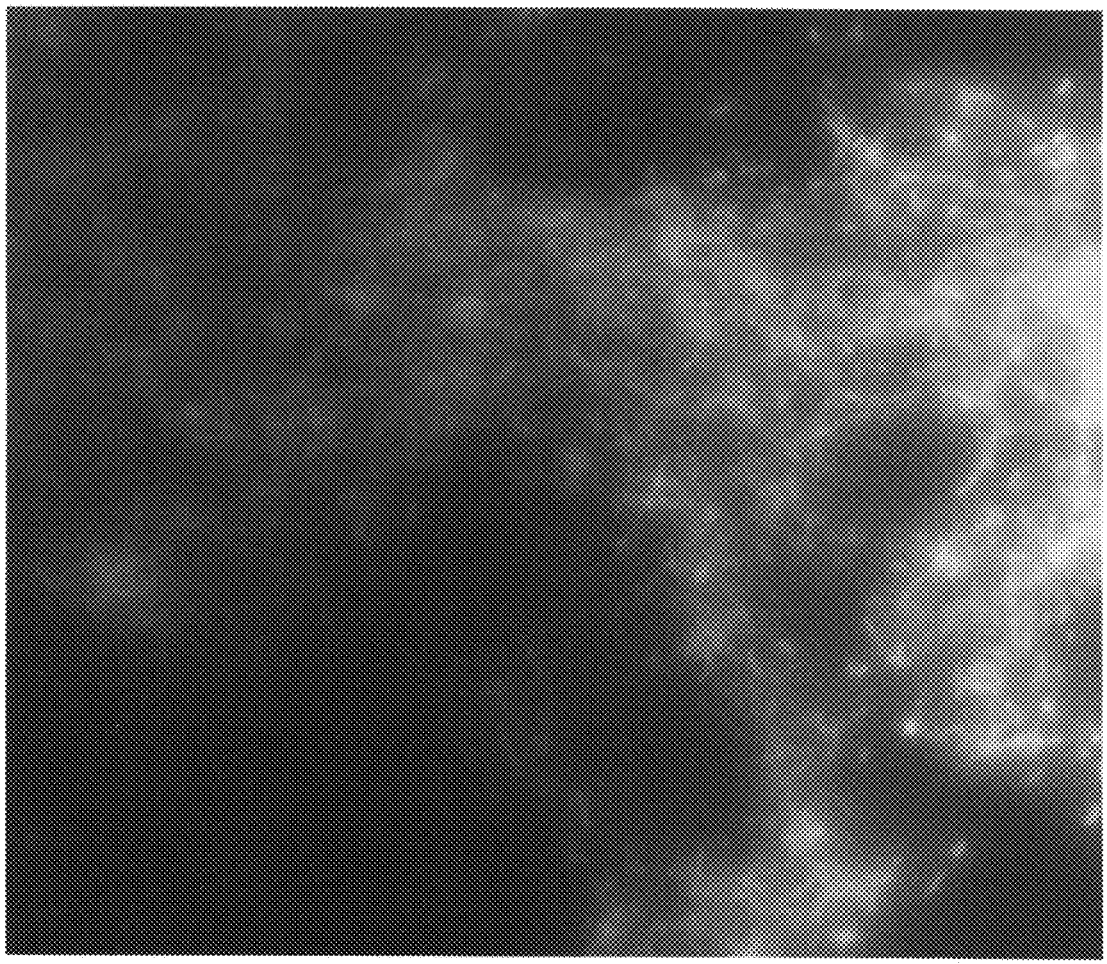
FIG. 7 shows BacLight DEAD/LIVE stained *Borrelia burgdorferi* on a collagen-coated slide. A single bacterial cell was spiked into 10 ml of human blood and cultured in Coplin jar with collagen-coated slides and BSK-H culture medium as described in Example 7. Green staining=live cells, red staining=dead cells. Magnification: 200×.

The culture techniques of Examples 2, 3, and 5 were verified using established *Borrelia burgdorferi* cell lines (B31 strain, passage 4, ATCC #35210). Peripheral blood samples (10 ml in red cap VACUTAINER™ tubes) from healthy volunteers were spiked with 0, 1, 10, 100 or 1000 *Borrelia* cells and stored at room temperature for 24 hours to mimic transfer time. Serum was isolated and long-term Coplin jar cultures were set up as described in Example 5. As early as 14 days of long-term culture, significant *Borrelia* growth was observed on every collagen-coated slide from a sample spiked with *Borrelia* cells. When sufficient cells had grown on the collagen-coated slides, one slide from each sample was stained with BacLight Live/Dead staining kit (Invitrogen). See, FIG. 7. The other slides were scraped and spirochete cells were counted under dark-field microscopy.

Each sample spiked with *Borrelia* cells (1, 10, 100, or 1000 cells) yielded significant spirochetal growth on the collagen-coated slide (between $1 \times 10^8$ and $2 \times 10^8$ cells per slide). Blood samples that were not spiked with *Borrelia* cells did not yield any spirochetes on the collagen-coated cells. These data support the hypothesis that the collagen matrix is beneficial for spirochete growth and confirm that the culture method of the present invention is sensitive enough to detect a single spirochete cell in a peripheral blood sample.

Example 8

Verifying the Culture Method

To determine the sensitivity of this culture method, a trial study was performed using serum samples from 72 Lyme disease patients, whose Lyme disease diagnosis was confirmed by a 2-tiered serological method following CDC testing guidelines. All patients were free of antibiotic therapy for a minimum of 4 weeks. To determine the specificity of the test, the culture method was performed using serum collected from 34 healthy controls with no tick-bite history. Patients and controls were selected from private practices in areas both endemic and non-endemic for Lyme disease from 14 different states (CA, AR, CT, NH, NJ, NY, MA, MD, MN, OR, PA, TN, UT, VT) from October 2011 to May 2012.

Figure 8:
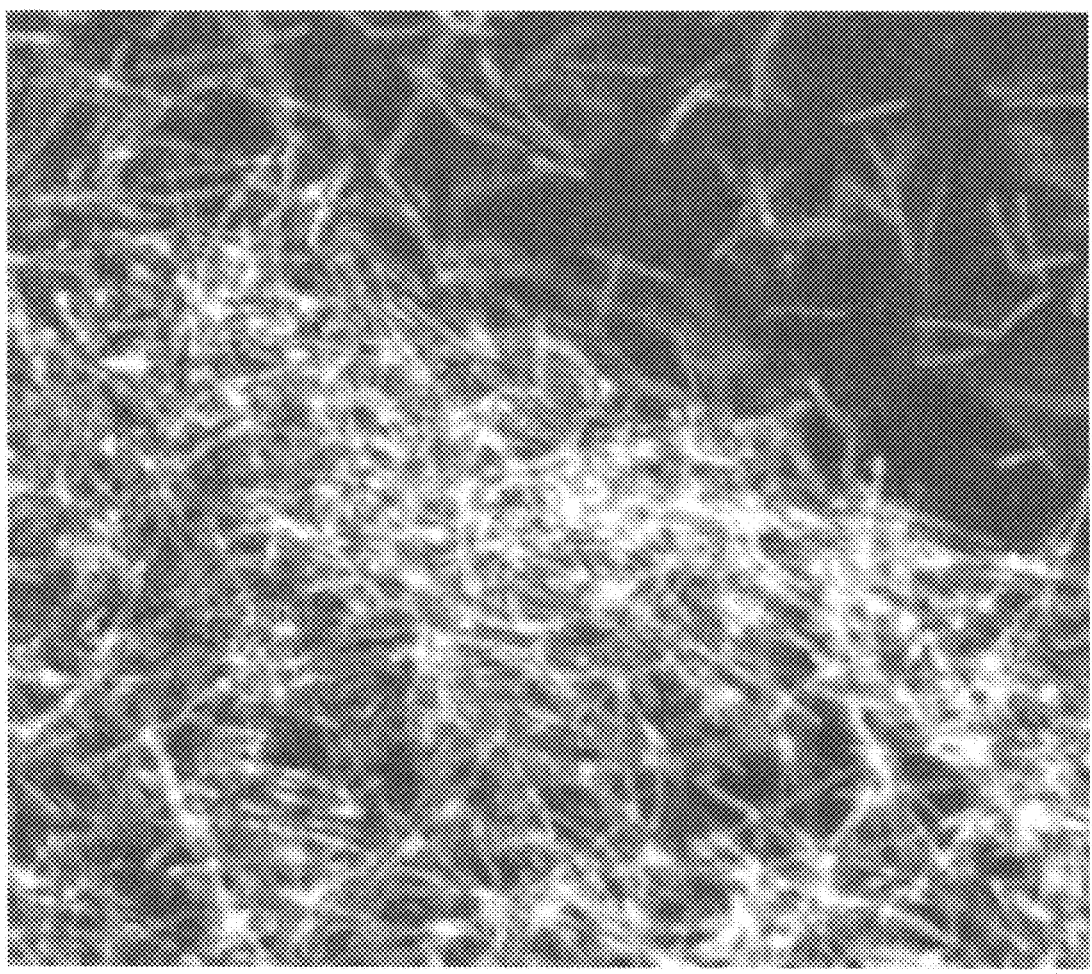
FIG. 8 shows a dark-field microscopy image of a sample from a CDC positive Lyme disease patient which was cultured with the method of the invention. Spirochete colonies can be observed on the collagen-coated slides. Magnification 400×
Figure 9:
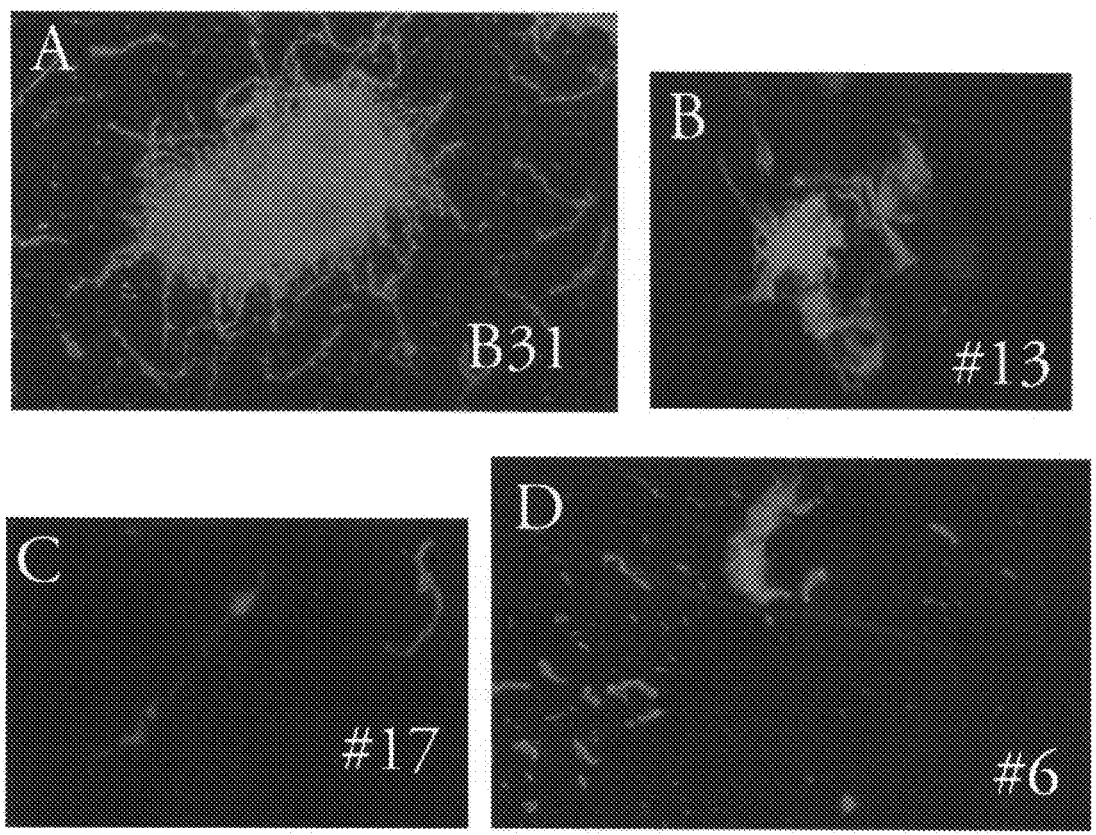
FIG. 9 shows immunohistochemistry images of clinical samples from 3 patients diagnosed with Lyme disease. The samples were cultured with the method of the invention and immunostained with fluorescent antibodies against *Borrelia burgdorferi*. Panel A: positive control *Borrelia burgdorferi* B31 strain, Panel B-D: Patient samples #13, #17, and #6, respectively.

All serum samples were cultured as described in Example 5 above and all of the cultures were first analyzed by dark-field microscopy (FIG. 8) and immunohistochemical staining techniques using monoclonal and polyclonal antibodies specific for *Borrelia* spp (PA1-73004 Thermo scientific) or for *Borrelia burgdorferi* sensu stricto (MA-1-7006AB, Thermo scientific) (FIG. 9). Positive samples were confirmed by PCR using primers for 16S ribosomal DNA (specific for *Borrelia* sensu lato), as well as primers for CTP synthase (PyrG, a housekeeping gene target sequence for *Borrelia burgdorferi* sensu stricto). All positive PCR results were further confirmed by direct sequencing. The results were statistically analyzed using the modified Wald method with a 95% confidence interval.

Figure 10:
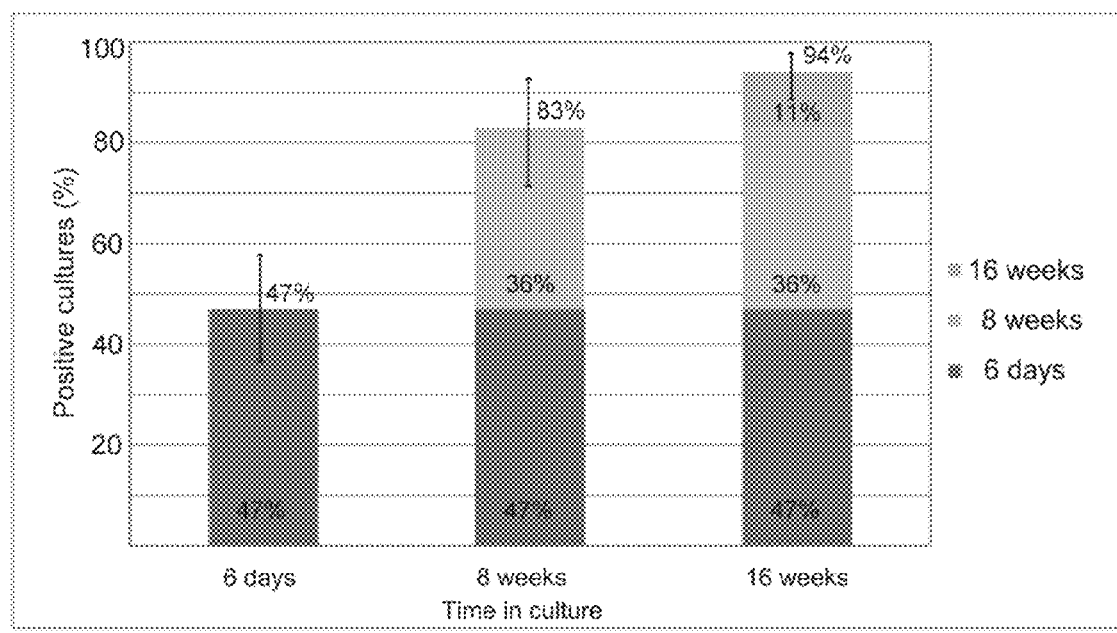
FIG. 10 summarizes the percentage of the successful *Borrelia burgdorferi* cultures of the clinical samples from 72 Lyme disease patients whose diagnosis was supported by the 2-tiered serological method that follows the CDC surveillance testing guidelines. The samples were cultured with the method of the present invention for 6 days, 8 weeks and 16 weeks, and the cultures were confirmed to be *Borrelia burgdorferi* species by immunocytochemical and PCR methodologies. 34 of the 72 cultures were positive after 6-days of culturing (47% with a 95% confidence interval of 36%-58%). An additional 26 samples showed spirochetal presence at 8 weeks of culture (83% with a 95% confidence interval of 72%-92%). At 16 weeks, an additional 8 samples became positive for spirochetal growth (94% with a 95% confidence interval of 86%-97%). The confidence interval values are depicted by vertical lines.

After a short-term 6-day culture, 34 of the 72 Lyme patient cultures were positive for spirochetes by immunohistochemical staining (47% of samples positive with a 95% confidence interval of 36%-58%). See, FIG. 10. A long-term culture was established from each patient sample, which was further analyzed after 8 weeks. An additional 26 samples showed spirochetal presence at 8 weeks of culture (83% of samples positive with a 95% confidence interval of 72%-92%). See, FIG. 10. At 16 weeks, an additional 8 samples became positive for spirochetal growth (94% of samples positive with a 95% confidence interval of 86%-97%). See, FIG. 10. All of the positive samples stained positively with both monoclonal and polyclonal antibodies (FIG. 9) and all were positive in PCR assays using target sequences for 16S ribosomal DNA sequences and/or CTP synthase housekeeping genes. Sequence analyses further confirmed the presence of *Borrelia burgdorferi* DNA with 93-100% identity to the published *Borrelia burgdorferi* sensu stricto sequences. Sequence variation at the CTP synthase gene locus was identified among the samples sequenced indicating that samples were derived from independent sources and not from laboratory contamination.

All 34 negative control samples were negative at all time points we examined (6 days, 8 weeks and 16 weeks); 100% with 95% confidence interval of 91%-100%). These data confirm that the culture and diagnostic methods of the present invention reliably and specifically diagnose spirochete infections.

What is claimed is:

1. An in vitro method of culturing a spirochete comprising:
   (1) inoculating a spirochete culture medium with the spirochete to generate a first culture;
   (2) incubating the first culture in a first culture vessel in about 3-5% $CO_2$ for about 4-6 days; and
   (3) optionally, evaluating the first culture for the presence of spirochetes; and
   (4) after incubating the first culture in about 3-5% $CO_2$ for about 4-6 days, contacting the $CO_2$ incubated first culture with a matrix-coated support.

2. The method according to claim 1, wherein the spirochete culture medium comprises a spirochete-supporting medium, serum, a reducing agent, and an antibiotic.

3. The method according to claim 2, wherein the spirochete-supporting medium is selected from BSK-H medium and BSK-II medium.

4. The method according to claim 2, wherein the serum is rabbit serum.

5. The method according to claim 2, wherein the serum concentration is about 6-12%.

6. The method according to claim 5, wherein the serum concentration is 12%.

7. The method according to claim 2, wherein the reducing agent is dithiothreitol (DTT).

8. The method according to claim 7, wherein the DTT is present at a concentration of about 0.1-100 μg/ml.

9. The method according to claim 2, wherein the antibiotic is rifampicin.

10. The method according to claim 9, wherein the rifampicin is present (1) at a concentration of 1 μg/ml or (2) as an antibiotics disc.

11. The method according to claim 2, wherein the spirochete culture medium comprises BSK-H, 12% rabbit serum, 100 μg/ml DTT, and 1 μg/ml rifampicin.

12. The method according to claim 2, wherein the spirochete culture medium comprises BSK-H, 12% rabbit serum, 100 μg/ml DTT, and a rifampicin antibiotic disc.

13. The method according to claim 1, wherein gas exchange between the first culture and the environment is permitted, optionally to a limited extent.

14. The method according to claim 1, wherein the first culture vessel has a lid and the lid either (1) is loose or (2) comprises a vent.

15. The method according to claim 1, wherein the first culture is incubated at about 32-36° C.

16. The method according to claim 1, wherein the first culture is incubated in about 5% $CO_2$.

17. The method according to claim 1, wherein the first culture is incubated in about 96-100% humidity.

18. The method according to claim 1, wherein the contacting step is performed by transferring said $CO_2$ incubated spirochete cells into a second culture vessel, wherein the second culture vessel contains a spirochete culture medium, comprising a spirochete-supporting medium, serum, a reducing agent, and an antibiotic and one or more solid supports coated with the matrix to generate a second culture; and further comprising:
   (5) incubating the second culture in about 3-5% $CO_2$ for at least about 4-8 weeks.

19. The method according to claim 18, wherein the matrix is collagen.

20. The method according to claim 18, wherein the solid support is a collagen-coated slide.

21. The method according to claim 18, wherein gas exchange between the second culture medium and the environment is permitted, optionally to a limited extent.

22. The method according to claim 21, wherein the second culture vessel has a lid that either (1) is loose or (2) comprises a vent.

23. The method according to claim 18, wherein the second culture is incubated at about 32-36° C.

24. The method according to claim 18, wherein the second culture is incubated in about 5% $CO_2$.

25. The method according to claim 18, wherein the second culture is incubated in about 96-100% humidity.

26. The method according to claim 1, wherein the spirochete is *Borrelia burgdorferi, Borrelia recurrentis, Treponema pallidum, Brachyspira pilosicoli*, or *Brachyspira aalborgi*.

27. The method according to claim 26, wherein the spirochete is *Borrelia burgdorferi*.

28. The method according to claim 1, wherein the spirochete is obtained from a sample from a subject suffering from a spirochete infection.

29. The method according to claim 1, wherein the first culture is incubated in an anaerobic environment.

30. The method according to claim 1, wherein the first culture is incubated at about 32-36° C. in about 3-5% $CO_2$ and about 96-100% humidity.

31. The method according to claim 1, wherein the first culture vessel is a polystyrene tube.

32. The method according to claim 31, wherein the polystyrene tube has a volume less than about 5 ml.

33. The method according to claim 32, wherein the polystyrene tube has a volume of about 2 ml.

34. The method according to claim 33, wherein the first culture has a volume of about 1.8 ml.

35. The method according to claim 18, wherein the second culture is incubated at about 32-36° C. in about 3-5% $CO_2$ and about 96-100% humidity.

36. The method according to claim 18, wherein the second culture vessel is a Coplin jar.

37. The method according to claim 28, wherein the subject is human.

38. The method according to claim 28, wherein the sample is a skin biopsy, a cerebrospinal fluid sample, a joint fluid sample or a blood sample.

39. The method according to claim 38, wherein the blood sample is drawn after noon.

40. The method according to claim 18, wherein the second culture is incubated in an anaerobic environment.

41. The method according to claim 29, wherein the anaerobic environment is obtained by culturing spirochetes in a culture volume that is about 90% of the culture vessel volume, candle extinction in a sealed jar, flushing with inert gas, or addition of an additional reducing agent.

42. The method according to claim 40, wherein the anaerobic environment is obtained by culturing spirochetes in a culture volume that is about 90% of the culture vessel volume, candle extinction in a sealed jar, flushing with inert gas, or addition of an additional reducing agent.

* * * * *